(12) United States Patent
Kanai et al.

(10) Patent No.: US 7,168,850 B2
(45) Date of Patent: Jan. 30, 2007

(54) MIRROR SURFACE STATE DETECTION DEVICE AND MOISTURE DETECTION DEVICE

(75) Inventors: Yoshiyuki Kanai, Tokyo (JP);
Kazumasa Ibata, Tokyo (JP); Shigeki Shoji, Tokyo (JP); Masaki Takechi, Tokyo (JP); Zentaro Nakamura, Tokyo (JP); Masahiro Komatsu, Tokyo (JP); Shingo Masumoto, Tokyo (JP)

(73) Assignee: Yamatake Corporation, Tokyo (JP)

( * ) Notice: Subject to any disclaimer, the term of this patent is extended or adjusted under 35 U.S.C. 154(b) by 64 days.

(21) Appl. No.: 11/094,014

(22) Filed: Mar. 29, 2005

(65) Prior Publication Data

US 2005/0220166 A1 Oct. 6, 2005

(30) Foreign Application Priority Data

| Mar. 30, 2004 | (JP) | ............................ 2004-101413 |
| Oct. 29, 2004 | (JP) | ............................ 2004-317073 |
| Oct. 29, 2004 | (JP) | ............................ 2004-317074 |
| Oct. 29, 2004 | (JP) | ............................ 2004-317082 |

(51) Int. Cl.
*G01N 25/02* (2006.01)
(52) U.S. Cl. ............................ 374/27; 374/28; 374/16
(58) Field of Classification Search .................. 374/17, 374/18, 19, 20, 27, 28
See application file for complete search history.

(56) References Cited

U.S. PATENT DOCUMENTS 4,621,929 A 11/1986 Phillips

| 6,022,138 A | * | 2/2000 | Sonander | ...................... 374/28 |
| 6,164,817 A | * | 12/2000 | Trainer | ........................ 374/19 |
| 6,604,852 B1 | * | 8/2003 | Murphy et al. | ................ 374/20 |

FOREIGN PATENT DOCUMENTS

| JP | 61-075235 A | 4/1986 |
| JP | 63-309846 A | 12/1988 |
| JP | 3-287050 | 12/1991 |
| JP | 7-104304 | 4/1995 |
| JP | 8-240544 | 9/1996 |
| JP | 9-5266 | 1/1997 |
| JP | 11-14575 | 1/1999 |
| WO | WO 9201927 A1 * | 2/1992 |

OTHER PUBLICATIONS

"The Outline of Industrial Measurement Technology 10, Temperature/Moisture Measurement", Nikkan Kogyo Shimbun, pp. 87-91.

* cited by examiner

*Primary Examiner*—Diego Gutierrez
*Assistant Examiner*—Mirellys Jagan
(74) *Attorney, Agent, or Firm*—Blakely Sokoloff Taylor & Zafman

(57) ABSTRACT

In a mirror surface state detection device, a light-emitting element obliquely irradiates the mirror surface of a mirror with light. A light-receiving element is arranged adjacent to the light-emitting element to have an optical axis almost parallel to that of the light-emitting element and a tilt angle almost equal to that of the light-emitting element and receives scattered light of the light emitted from the light-emitting element. A condensation detection unit detects the state on the mirror surface on the basis of the scattered light received by the light-receiving element. A moisture detection device is also disclosed.

5 Claims, 14 Drawing Sheets

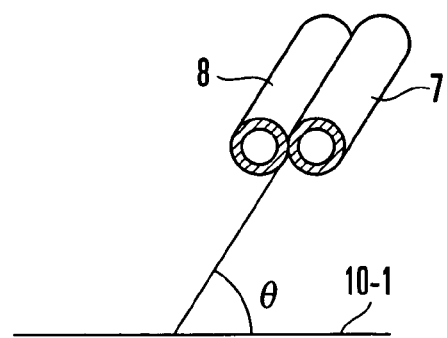
FIG. 2
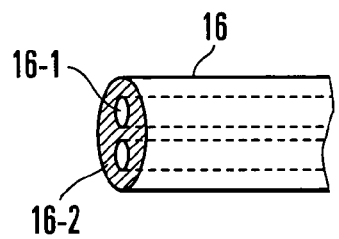
FIG. 3A
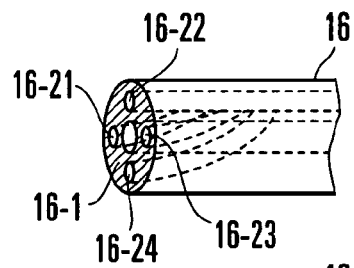
FIG. 3B
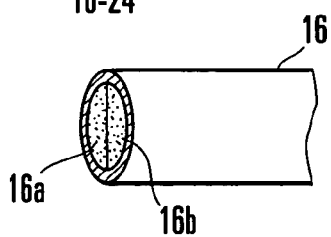
FIG. 3C
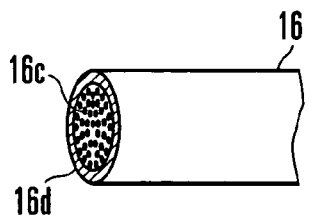
FIG. 3D
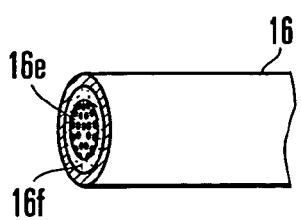
FIG. 3E
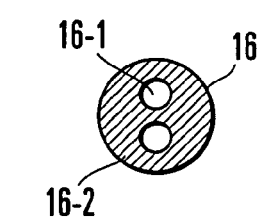
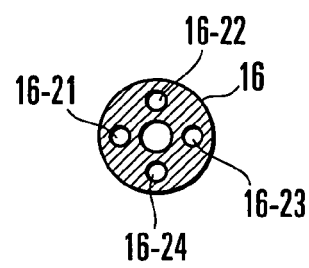
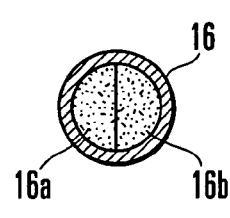
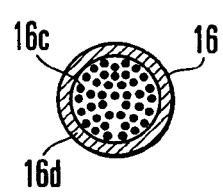
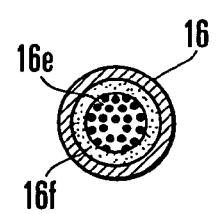

FIG. 5A
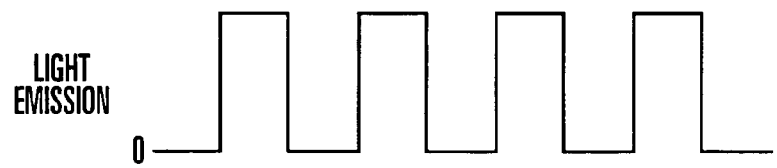
FIG. 5B
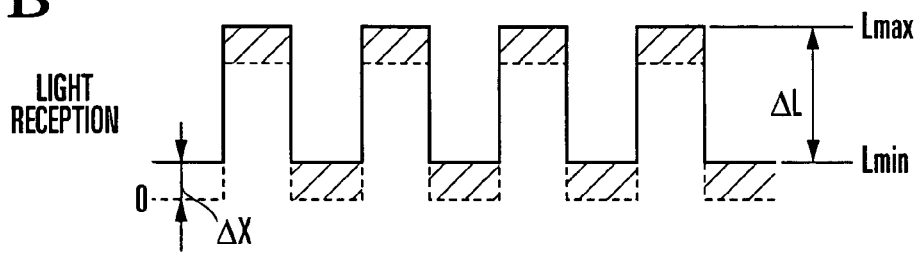
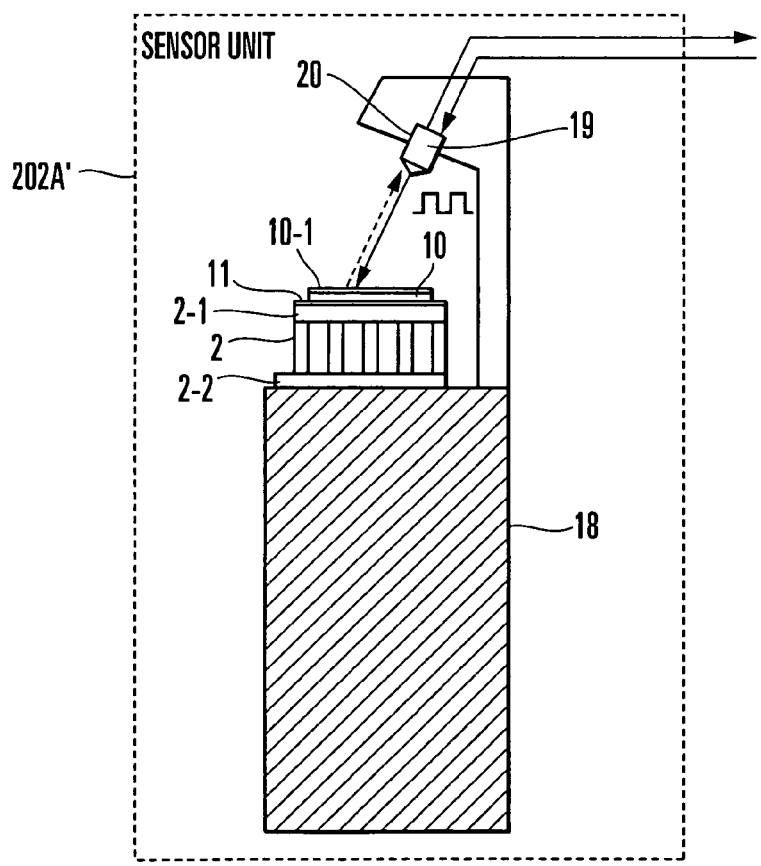
FIG. 6

MIRROR SURFACE STATE DETECTION DEVICE AND MOISTURE DETECTION DEVICE

BACKGROUND OF THE INVENTION

The present invention relates to a mirror surface state detection device which detects the state on a mirror surface and a moisture detection device which detects moisture contained in a target measurement gas condensed on the mirror surface.

Conventionally, as a humidity measuring method, a dew point detection method is known, in which the temperature of a target measurement gas is decreased, and the temperature at which vapor contained in the target measurement gas partially condenses is measured, thereby detecting the dew point. For example, "The Outline of Industrial Measurement Technology 10, Temperature/Moisture Measurement", Nikkan Kogyo Shimbun, pp. 87–91 (reference 1) describes a mirror surface cooling dew point detector which cools a mirror by using a freezing mixture, refrigerator, or electronic cooler, detects a change in intensity of reflected light on the mirror surface of the cooled mirror, and measures the temperature of the mirror surface at this time, thereby detecting the dew point of moisture in the target measurement gas.

Mirror surface cooling dew point detectors are classified into two types depending on the type of reflected light to be used. One type uses a regular-reflected light detection method using regular-reflected light proposed in Japanese Patent Laid-Open No. 61-75235. The other type uses a scattered light detection method using scattered light proposed in Japanese Patent Laid-Open No. 63-309846.

[Regular-Reflected Light Detection Method]

FIG. 18 shows the main part of a conventional mirror surface cooling dew point detector which employs the regular-reflected light detection method. A mirror surface cooling dew point detector 101 comprises a chamber 1 in which a target measurement gas flows and a thermoelectric cooling element (Peltier element) 2 provided in the chamber 1. A bolt 4 is attached to a cooled surface 2-1 of the thermoelectric cooling element 2 through a copper block 3. A radiating fin 5 is attached to a heated surface 2-2 of the thermoelectric cooling element 2. An upper surface 4-1 of the bolt 4 attached to the copper block 3 is a mirror surface.

A wire-wound resistance thermometer sensor (temperature detection element) 6 is embedded in the side part of the copper block 3 (FIG. 22). A light-emitting element 7 which obliquely irradiates the upper surface (mirror surface) 4-1 of the bolt 4 with light and a light-receiving element 8 which receives the regular-reflected light of light emitted from the light-emitting element 7 to the mirror surface 4-1 are provided at the upper portion of the chamber 1. A heat insulator 40 is provided around the thermoelectric cooling element 2.

In the mirror surface cooling dew point detector 101, the mirror surface 4-1 in the chamber 1 is exposed to the target measurement gas flowing into the chamber 1. If no condensation occurs on the mirror surface 4-1, the light emitted from the light-emitting element 7 is almost wholly regularly reflected and received by the light-receiving element 8. Hence, when no condensation occurs on the mirror surface 4-1, the intensity of reflected light received by the light-receiving element 8 is high.

As the current to the thermoelectric cooling element 2 is increased to lower the temperature of the cooled surface 2-1 of the thermoelectric cooling element 2, vapor contained in the target measurement gas condenses on the mirror surface 4-1. The light emitted from the light-emitting element 7 is partially absorbed or diffused by the molecules of water. The intensity of the reflected light (regular-reflected light) received by the light-receiving element 8 decreases. When the change in regular-reflected light on the mirror surface 4-1 is detected, the change of the state on the mirror surface 4-1, i.e., adhesion of moisture (water droplets) on the mirror surface 4-1 can be recognized. In addition, when the temperature of the mirror surface 4-1 at this time is measured indirectly by the temperature detection element 6, the dew point of moisture in the target measurement gas can be detected.

[Scattered Light Detection Method]

FIG. 19 shows the main part of another conventional mirror surface cooling dew point detector which employs the scattered light detection method. A mirror surface cooling dew point detector 102 has almost the same arrangement as the mirror surface cooling dew point detector 101 using the regular-reflected light detection method except the mount position of the light-receiving element 8. In the mirror surface cooling dew point detector 102, the light-receiving element 8 is provided not at the position to receive the regular-reflected light of light emitted from the light-emitting element 7 to the mirror surface 4-1 but at the position to receive scattered light.

In the mirror surface cooling dew point detector 102, the mirror surface 4-1 is exposed to the target measurement gas flowing into the chamber 1. If no condensation occurs on the mirror surface 4-1, the light emitted from the light-emitting element 7 is almost wholly regularly reflected, and the amount of light received by the light-receiving element 8 is very small. Hence, when no condensation occurs on the mirror surface 4-1, the intensity of reflected light received by the light-receiving element 8 is low.

As the current to the thermoelectric cooling element 2 is increased to lower the temperature of the cooled surface 2-1 of the thermoelectric cooling element 2, vapor contained in the target measurement gas condenses on the mirror surface 4-1. The light emitted from the light-emitting element 7 is partially absorbed or diffused by the molecules of water. The intensity of the diffused light (scattered light) received by the light-receiving element 8 increases. When the change in scattered light on the mirror surface 4-1 is detected, the change of the state on the mirror surface 4-1, i.e., adhesion of moisture (water droplets) on the mirror surface 4-1 can be recognized. In addition, when the temperature of the mirror surface 4-1 at this time is measured indirectly by the temperature detection element 6, the dew point of moisture in the target measurement gas can be detected.

In the above-described dew point detectors, condensation (moisture) on the mirror surface 4-1 is detected. With the same arrangement as described above, frost (moisture) on the mirror surface 4-1 can also be detected.

The arrangement shown in FIG. 20 or 22 can also be employed. More specifically, the thermoelectric cooling element 2 and temperature detection element 6 are omitted. Only a mirror 9 is provided in the chamber 1. An opening portion is provided in the upper surface of the chamber 1. In this case, the detector can be used as a mirror surface state detection device (weather detector) which detects moisture sticking to a mirror surface 9-1 when it begins to rain or snow. In a weather detector 103 or 104, when rain or snow falls into the chamber 1 and sticks to the mirror surface 9-1, it is detected on the basis of the intensity of reflected light received by the light-receiving element 8.

However, according to the above-described conventional mirror surface cooling dew point detector 101 or 102 or weather detector 103 or 104, the light-emitting element 7 and light-receiving element 8 are independently installed at different tilt angles such that they should maintain a predetermined positional relationship. For this reason, the chamber 1 inevitably becomes bulky, and size reduction cannot be promoted. Additionally, since the light-emitting element 7 and light-receiving element 8 are separately arranged at different angles, alignment between the light-emitting element 7 and the light-receiving element 8 in assembly is difficult, resulting in poor workability.

In the mirror surface cooling sensor 101 or 102 shown in FIG. 18 or 19, the lower limit of dew point measurement is determined by how low the temperature of the cooled surface 2-1 of the thermoelectric cooling element 2 can be made. For this reason, in another mirror surface cooling sensor, to further cool the cooled surface 2-1 of the thermoelectric cooling element 2, one end of a heat pipe is attached to the heated surface 2-2 of the thermoelectric cooling element 2. The radiating member 5 is attached to the other end of the heat pipe spaced apart from the thermoelectric cooling element 2. With this structure, heat generated in the heated surface 2-2 moves from one end to the other end of the heat pipe and dissipated through the radiating member 5. In addition, by providing the heat insulating member, the heat from the heated surface 2-2 of the thermoelectric cooling element 2 and the heat pipe is prevented from returning to the chamber 1 and mirror member.

In the above-described mirror surface cooling sensor, the light-emitting element 8 and light-receiving element 9 are fixed in the chamber 1. A lead wire is connected to the thermoelectric cooling element 2 through the heat insulating member integrally fixed to the heat pipe. For this reason, it is difficult to exchange the light-emitting element 8, light-receiving element 9, or thermoelectric cooling element 2 on the site. In addition, position adjustment of the mirror member, light-emitting element 8, or light-receiving element 9 on the site is difficult. For mirror surface cooling sensors of this type, it is demanded to facilitate maintenance such as adjustment and exchange of components in the sensor to cope with the environmental difference of the installation site or the difference of required measurement accuracy.

SUMMARY OF THE INVENTION

It is an object of the present invention to provide a mirror surface state detection device and moisture detection device capable of prompting size reduction.

It is another object of the present invention to provide a mirror surface state detection device and moisture detection device capable of increasing the workability in assembly.

It is still another object of the present invention to provide a mirror surface state detection device and moisture detection device capable of easily executing maintenance on the site.

In order to achieve the above objects, according to the present invention, there is provided a mirror surface state detection device comprising light-emitting means for obliquely irradiating a mirror surface of a mirror with light, light-receiving means, arranged adjacent to the light-emitting means to have an optical axis substantially parallel to an optical axis of the light-emitting means and a tilt angle substantially equal to a tilt angle of the light-emitting means, for receiving scattered light of the light emitted from the light-emitting means to the mirror surface, and a mirror surface state detection means for detecting a state on the mirror surface on the basis of the scattered light received by the light-receiving means.

BRIEF DESCRIPTION OF THE DRAWINGS

FIG. 2 is a view showing the arrangement of a light-emitting element and light-receiving element in the mirror surface cooling dew point detector shown in FIG. 1;

FIGS. 3A to 3E are views showing arrangements in which a light-emitting-side optical fiber and light-receiving-side optical fiber are coaxially provided in one tube;

FIG. 5A is a graph showing pulse light with which the mirror surface of the mirror surface cooling dew point detector shown in FIG. 2 is irradiated;

FIG. 5B is a graph showing reflected pulse light (scattered light) received from the mirror surface;

FIG. 6 is a view showing a modification of the sensor unit of the mirror surface cooling dew point detector shown in FIG. 4;

DESCRIPTION OF THE PREFERRED EMBODIMENTS

The present invention will be described below in detail with reference to the accompanying drawings.

First Embodiment: Mirror Surface Cooling Dew Point Detector (With Chamber)

Figure 1:
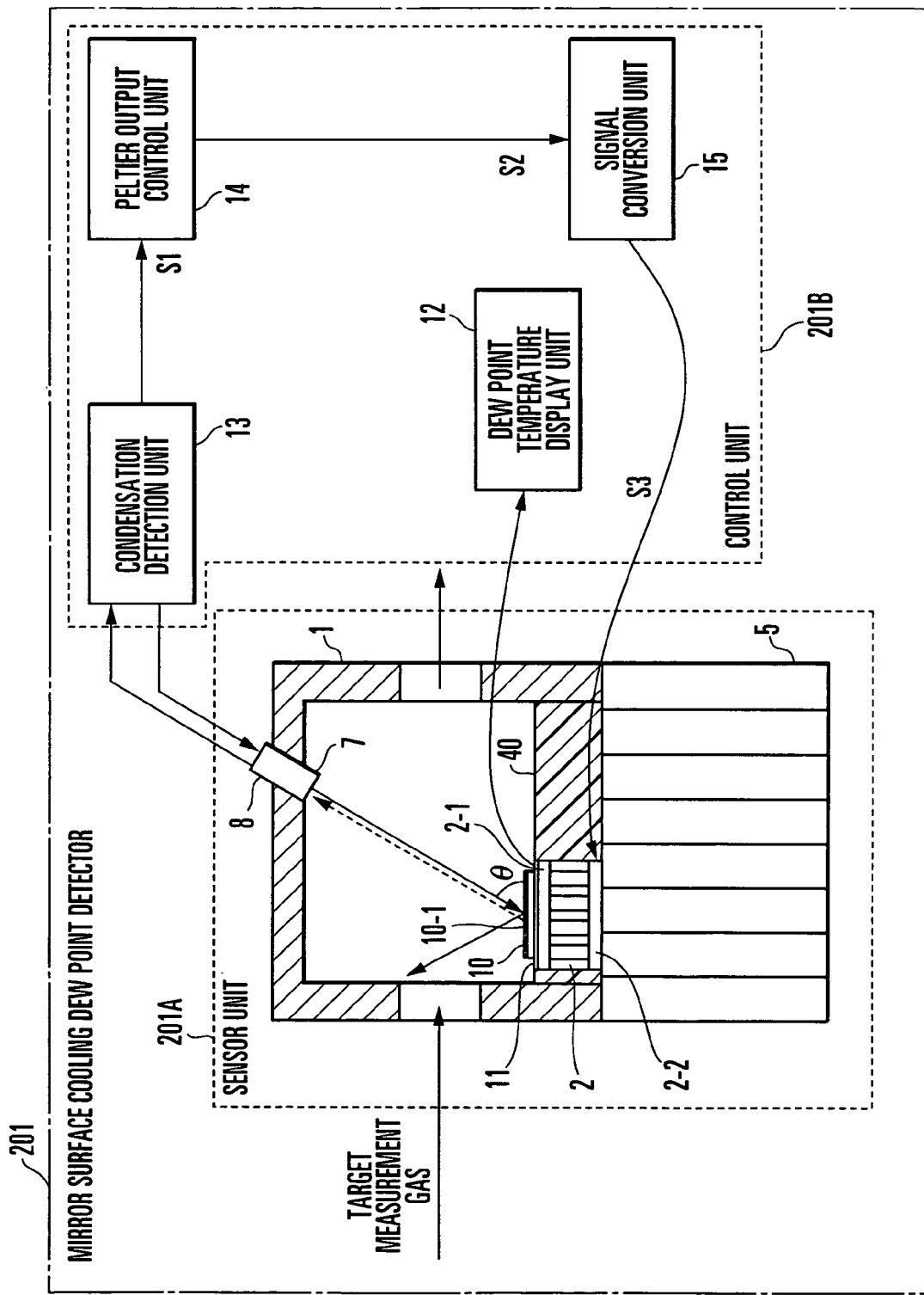
FIG. 1 is a schematic view showing the arrangement of a mirror surface cooling dew point detector (moisture detection device) according to the first embodiment of the present invention.

FIG. 1 shows the schematic arrangement of a mirror surface cooling dew point detector (moisture detection device) according to the first embodiment of the present invention. A mirror surface cooling dew point detector 201 has a sensor unit 201A and control unit 201B.

In the sensor unit 201A, a light-emitting element 7 and light-receiving element 8 are arranged adjacent in parallel at the same tilt angle θ in a chamber 1, as shown in FIG. 2. More specifically, the irradiation direction (optical axis) of the light-emitting element 7 and the light-receiving direction (optical axis) of the light-receiving element 8 are set parallel. The light-emitting element 7 and light-receiving element 8 are arranged adjacent at the same tilt angle, thereby attaching the elements to one point. A mirror 10 is attached to a cooled surface 2-1 of a thermoelectric cooling element (Peltier element) 2. The mirror 10 is formed from, e.g., a silicon chip whose surface 10-1 is a mirror surface. A thin-film resistance thermometer sensor (temperature detection element) 11 made of, e.g., platinum is formed on the bonding interface between the mirror 10 and the cooled surface 2-1 of the thermoelectric cooling element 2.

The control unit 201B includes a dew point temperature display unit 12, condensation detection unit 13, Peltier output control unit 14, and signal conversion unit 15. The temperature of the mirror 10 detected by the temperature detection element 11 is displayed on the dew point temperature display unit 12. The condensation detection unit 13 always turns on the light-emitting element 7 and sends a signal S1 corresponding to the reflected light intensity to the Peltier output control unit 14. Upon receiving the signal S1, the Peltier output control unit 14 compares the intensity of the reflected light received by the light-receiving element 8 with a predetermined threshold value.

If the reflected light intensity is less than the threshold value, the Peltier output control unit 14 outputs, to the signal conversion unit 15, a control signal S2 to increase the current to the thermoelectric cooling element 2 in accordance with the value of the signal S1. If the reflected light intensity exceeds the threshold value, the Peltier output control unit 14 outputs, to the signal conversion unit 15, the control signal S2 to decrease the current to the thermoelectric cooling element 2 in accordance with the value of the signal S1. The signal conversion unit 15 supplies, to the thermoelectric cooling element 2, a current S3 indicated by the control signal S2 from the Peltier output control unit 14.

In the mirror surface cooling dew point detector 201, the mirror surface 10-1 in the chamber 1 is exposed to the target measurement gas flowing into the chamber 1. If no condensation occurs on the mirror surface 10-1, light emitted from the light-emitting element 7 is almost wholly regularly reflected, and the amount of light received by the light-receiving element 8 is very small. Hence, when no condensation occurs on the mirror surface 10-1, the intensity of reflected light received by the light-receiving element 8 is low.

The condensation detection unit 13 sends, to the Peltier output control unit 14, the signal S1 corresponding to the intensity of the reflected light received by the light-receiving element 8. In this case, the reflected light intensity is almost zero and less than the threshold value. For this reason, the Peltier output control unit 14 sends, to the signal conversion unit 15, the control signal S2 to increase the current to the thermoelectric cooling element 2. With this operation, the current S3 from the signal conversion unit 15 to the thermoelectric cooling element 2 increases, and the temperature of the cooled surface 2-1 of the thermoelectric cooling element 2 becomes low.

As the temperature of the cooled surface 2-1 of the thermoelectric cooling element 2, i.e., the temperature of the mirror 10 is decreased, vapor contained in the target measurement gas condenses on the mirror surface 10-1 of the mirror 10. The light emitted from the light-emitting element 7 is partially absorbed or diffused by the molecules of water. The intensity of the reflected light (scattered light) received by the light-receiving element 8 increases. The condensation detection unit 13 sends the signal S1 corresponding to the reflected light intensity to the Peltier output control unit 14.

The Peltier output control unit 14 compares the intensity of the reflected light received by the light-receiving element 8 with a predetermined threshold value. If the intensity of the reflected light received by the light-receiving element 8 exceeds the threshold value, the Peltier output control unit 14 sends, to the signal conversion unit 15, the control signal S2 to decrease the current to the thermoelectric cooling element 2. With this operation, the decrease in temperature of the cooled surface 2-1 of the thermoelectric cooling element 2 is suppressed, and condensation is suppressed. When condensation is suppressed, the intensity of the reflected light received by the light-receiving element 8 becomes low. When the reflected light intensity is less than the threshold value, the Peltier output control unit 14 sends, to the signal conversion unit 15, the control signal S2 to increase the current to the thermoelectric cooling element 2.

By repeating this operation, the temperature of the cooled surface 2-1 of the thermoelectric cooling element 2 is adjusted so that the intensity of reflected light received by the light-receiving element 8 almost equals the threshold value. The adjusted temperature, i.e., the temperature (dew point temperature) at which condensation which has occurred on the mirror surface 10-1 reaches the equilibrium state is displayed on the dew point temperature display unit 12 as the dew point temperature.

In the mirror surface cooling dew point detector 201, the light-emitting element 7 and light-receiving element 8 are attached to one point, as described above. For this reason, the chamber 1 can be made smaller than in the conventional mirror surface cooling dew point detector 101 or 102, and the sensor unit 201A can be made compact. In addition, since the light-emitting element 7 and light-receiving element 8 are arranged adjacent in parallel at almost the same tilt angle, alignment is easy, and the workability in assembly increases.

In the mirror surface cooling dew point detector 201, a light-emitting diode (LED) can be used as the light-emitting element 7, and a photocoupler can be used as the light-receiving element 8. However, optical fibers can also be used. More specifically, a light-emitting-side optical fiber may be used as the light-emitting element 7, and a light-receiving-side optical fiber may be used as the light-receiving element 8. When the optical fibers are used, the light-emitting-side optical fiber and light-receiving-side optical fiber may coaxially be provided in one cable or tube. FIGS. 3A to 3E show arrangements in which the light-emitting-side optical fiber and light-receiving-side optical fiber are coaxially provided in one pipe (stainless tube).

Referring to FIG. 3A, a light-emitting-side optical fiber 16-1 and light-receiving-side optical fiber 16-2 are aligned along an axis in a tube 16. Referring to FIG. 3B, the light-emitting-side (or light-receiving-side) optical fiber 16-1 and light-receiving-side (or light-emitting-side) optical fibers 16-21 to 16-24 radially arranged with respect to the optical fiber 16-1 are provided in the tube 16. Referring to FIG. 3C, the left half in the tube 16 is formed from a light-emitting-side optical fiber 16a, and the right half is formed from a light-receiving-side optical fiber 16b. Referring to FIG. 3D, light-emitting-side optical fibers 16c and light-receiving-side optical fibers 16d are mixed in the tube 16. Referring to FIG. 3E, light-emitting-side (or light-receiving-side) optical fibers 16e are provided at the center of the tube 16, and a light-receiving-side (or light-emitting-side) optical fiber 16f is arranged around the optical fibers 16e.

Second Embodiment: Mirror Surface Cooling Dew Point Detector (Without Chamber)

In the mirror surface cooling dew point detector 201 shown in FIG. 1, the sensor unit 201A has the chamber 1. The chamber 1 is necessary for preventing any operation error by disturbance light (light shielding). Since the chamber 1 is present, the mirror surface cooling dew point detector 201 requires a suction pump or suction tube to draw the target measurement gas into the chamber 1, an exhaust tube, and a flowmeter. For this reason, the number of components is large, the sensor unit becomes bulky, and assembly is not easy.

Figure 4:
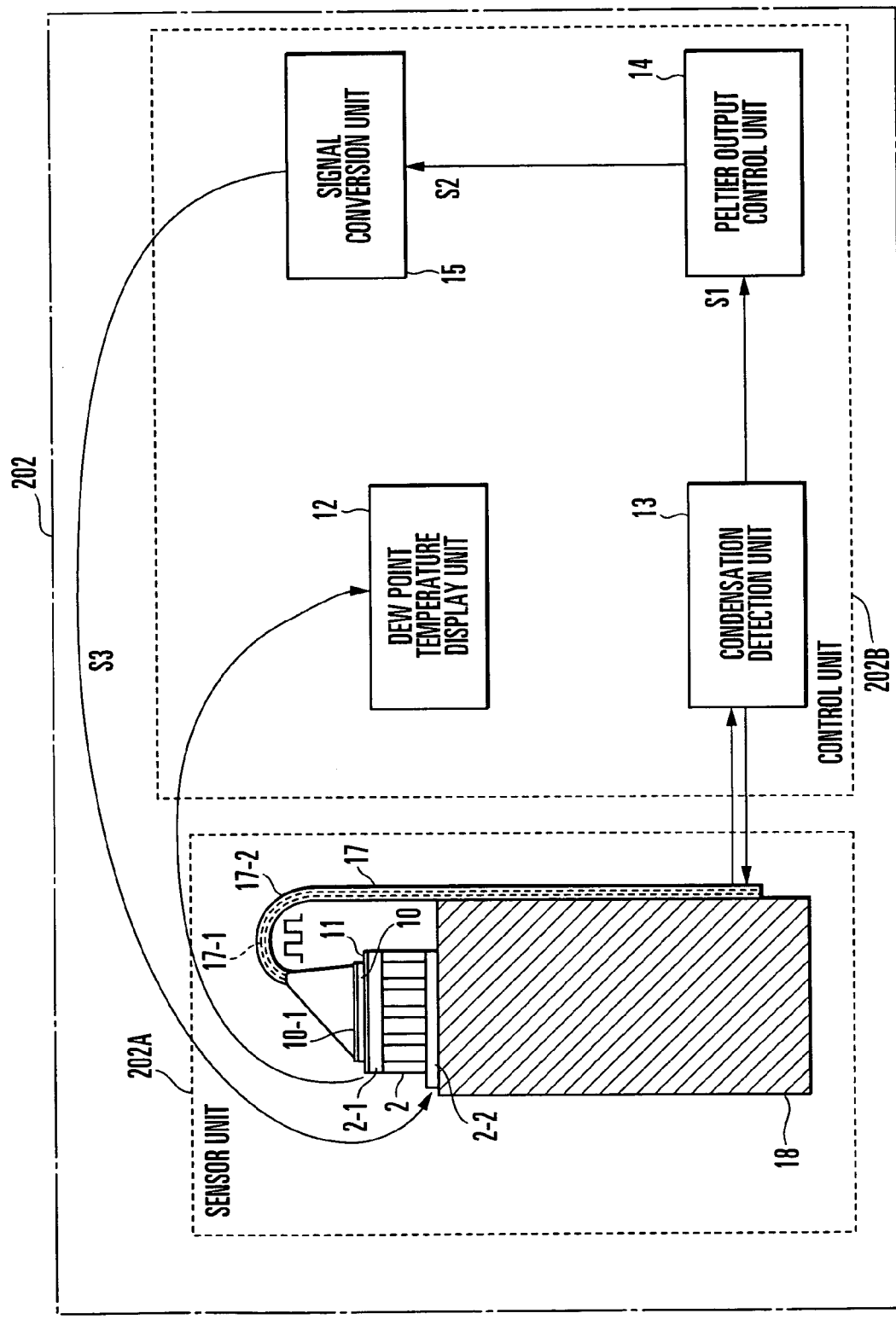
FIG. 4 is a schematic view showing the arrangement of a mirror surface cooling dew point detector (moisture detection device) according to the second embodiment of the present invention.

To solve this problem, a mirror surface cooling dew point detector 202 (FIG. 4) according to the second embodiment, a mirror surface 10-1 of a mirror 10 is obliquely irradiated with pulse light at a predetermined period. Condensation on the mirror surface 10-1 is detected on the basis of the difference between the upper limit value and lower limit value of one pulse of reflected pulse light (scattered light) received from the mirror surface 10-1. With this arrangement, the chamber 1 necessary in the mirror surface cooling dew point detector 201 of the first embodiment can be omitted. Hence, the suction pump or suction tube, exhaust tube, and flowmeter can be omitted.

In the mirror surface cooling dew point detector 202, a tube 17 with the upper end portion curved into a J-shape is provided in place of the light-emitting element 7 and light-receiving element 8 of the mirror surface cooling dew point detector 201 of the first embodiment. As the tube 17, the tube 16 which accommodates optical fibers in various forms as described with reference to FIGS. 3A to 3E can be used. In this embodiment, the tube 16 shown in FIG. 3A is used as the tube 17. The tube 17 incorporates a light-emitting-side optical fiber 17-1 and light-receiving-side optical fiber 17-2. The distal end portions (light-emitting portion and light-receiving portion) of the light-emitting-side optical fiber 17-1 and light-receiving-side optical fiber 17-2, which are curved into a J-shape, are directed to the mirror surface 10-1 of the mirror 10 and tilted at a predetermined tilt angle with respect to the mirror surface 10-1.

As a result, the light irradiation direction (optical axis) from the optical fiber 17-1 and the light-receiving direction (optical axis) on the optical fiber 17-2 are parallel. The optical fibers are arranged adjacent at the same tilt angle. In the mirror surface cooling dew point detector 202, instead of the radiating fin 5 of the mirror surface cooling dew point detector 101 of the first embodiment, a cylindrical heat sink 18 is bonded to a heated surface 2-2 of a thermoelectric cooling element 2. The tube 17 is provided along the heat sink 18.

In the mirror surface cooling dew point detector 202, a sensor unit 202A is placed on the target measurement gas. A condensation detection unit 13 causes the optical fiber 17-1 to obliquely irradiate the mirror surface 10-1 of the mirror 10 with pulse light from the tip at a predetermined period, as shown in FIG. 5A. The mirror surface 10-1 is exposed to the target measurement gas. If no condensation occurs on the mirror surface 10-1, the pulse light emitted from the tip of the optical fiber 17-1 is almost wholly regularly reflected. The amount of reflected pulse light (scattered light) received from the mirror surface 10-1 through the optical fiber 17-2 is very small. Hence, when no condensation occurs on the mirror surface 10-1, the intensity of reflected pulse light received through the optical fiber 17-2 is low.

On the other hand, when condensation occurs on the mirror surface 10-1, the pulse light emitted from the tip of the optical fiber 17-1 is partially absorbed or diffused by the molecules of water. The intensity of the reflected pulse light (scattered light) received from the mirror surface 10-1 through the optical fiber 17-2 increases.

The condensation detection unit 13 obtains the difference between the upper limit value and lower limit value of each pulse of the received reflected pulse light as the intensity of the reflected pulse light. More specifically, a difference $\Delta L$ between an upper limit value Lmax and lower limit value Lmin of one pulse of the reflected pulse light is obtained as the intensity of the reflected pulse light. By the processing by the condensation detection unit 13, disturbance light $\Delta X$ contained in the reflected pulse light is removed. Hence, any operation error by disturbance light can be prevented. The processing scheme by the condensation detection unit 13 using pulse light to prevent any operation error by disturbance light is called a pulse modulation scheme. With this processing, the chamber of the sensor unit 202A can be omitted from the mirror surface cooling dew point detector 202.

Even in the mirror surface cooling dew point detector 202, the light-emitting-side optical fiber 17-1 and light-receiving-side optical fiber 17-1 are attached to one point and contribute to size reduction of the detection unit 202A. The light-emitting-side optical fiber 17-1 and light-receiving-side optical fiber 17-2 are accommodated in one tube 17. Hence, no alignment is necessary between the light-emitting-side optical fiber 17-1 and light-receiving-side optical fiber 17-2, resulting in high workability in assembly. In the mirror surface cooling dew point detector 202, the sensor unit 202A has no chamber, and the suction pump or suction tube, exhaust tube, and flowmeter can be omitted. For this reason, the number of components is decreased, the sensor unit 202A can be made more compact, assembly is easy, and the cost can be reduced. Furthermore, the mirror surface cooling dew point detector can easily be installed in the measurement atmosphere.

In the mirror surface cooling dew point detector 202, the sensor unit 202A uses the tube 17 which accommodates the light-emitting-side optical fiber 17-1 and light-receiving-side optical fiber 17-2. Instead, as in a sensor unit 202A' shown in FIG. 6, a light-emitting diode 19 may be provided in place of the light-emitting-side optical fiber 17-1, and a photocoupler 20 may be provided in place of the light-receiving-side optical fiber 17-2.

In the above-described first and second embodiments, condensation (moisture) on the mirror surface 10-1 is detected. With the same arrangement as described above, frost (moisture) on the mirror surface 10-1 can also be detected. In the above-described first and second embodiments, the thermoelectric cooling element (Peltier element) 2 is used as the cooling means for cooling the mirror 10. However, a helium refrigerator may be used.

Third Embodiment: Weather Detector (With Chamber)

Figure 7:
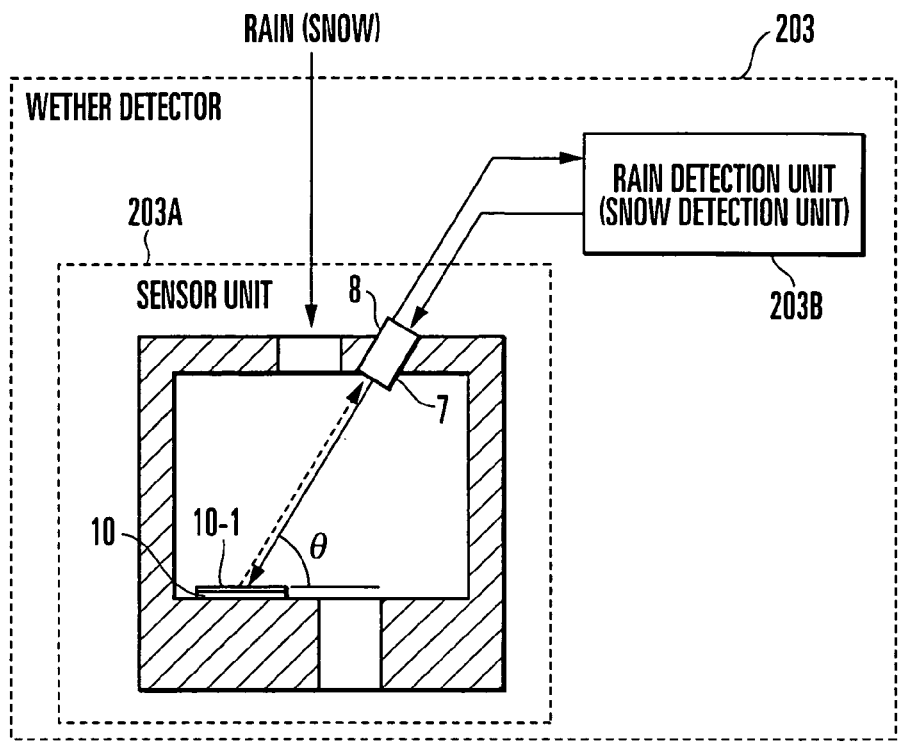
FIG. 7 is a schematic view showing the arrangement of a mirror surface state detection device (weather detector) according to the third embodiment of the present invention.

FIG. 7 shows the schematic arrangement of a mirror surface state detection device (weather detector) according to the third embodiment of the present invention. A weather detector 203 has a sensor unit 203A and rain detection unit 203B. In the sensor unit 203A, only a mirror 10 is provided in a chamber 1. As in the first embodiment, a light-emitting element 7 and light-receiving element 8 are arranged adjacent in parallel at the same tilt angle θ in the chamber 1.

In the weather detector 203, the rain detection unit 203B always turns on the light-emitting element 7. In addition, the rain detection unit 203B compares the intensity of reflected light received by the light-receiving element 8 with a predetermined threshold value. If the reflected light intensity exceeds the threshold value, it is determined that it begins to rain (rain sticks to a mirror surface 10-1).

Fourth Embodiment: Weather Detector (Without Chamber)

Figure 8:
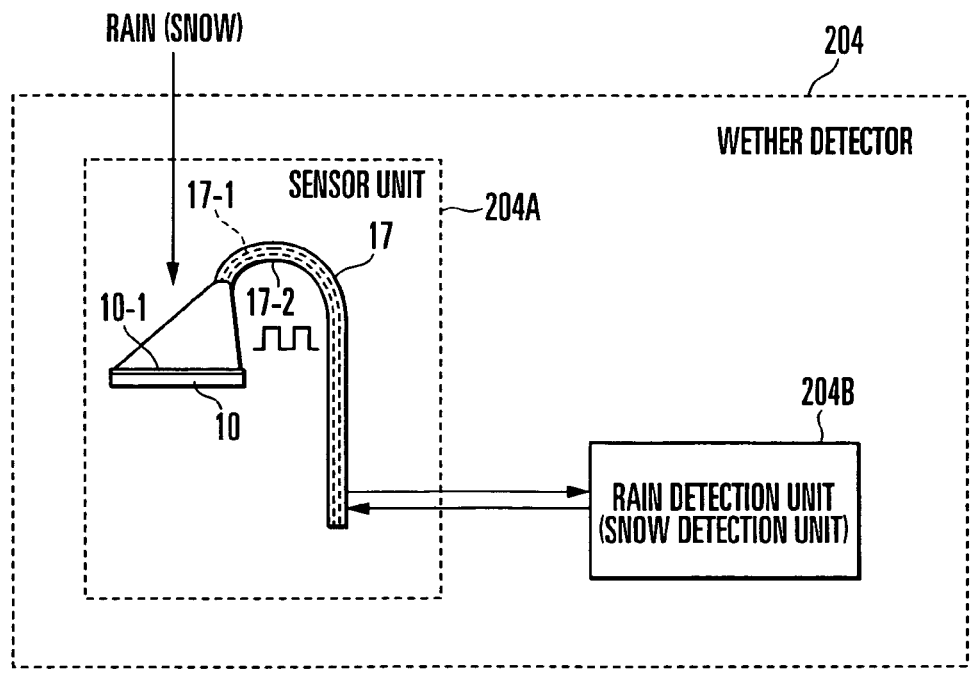
FIG. 8 is a schematic view showing the arrangement of a mirror surface state detection device (weather detector) according to the fourth embodiment of the present invention.

FIG. 8 shows the schematic arrangement of a mirror surface state detection device (weather detector) according to the fourth embodiment of the present invention. A weather detector 204 has a sensor unit 204A and rain detection unit 204B. In the sensor unit 204A, only a mirror 10 is provided. As in the second embodiment, a tube 17 with the upper end portion curved into a J-shape is provided.

In the weather detector 204, the rain detection unit 204B causes a light-emitting-side optical fiber 17-1 to obliquely irradiate a mirror surface 10-1 of the mirror 10 with pulse light at a predetermined period. In addition, the rain detection unit 204B obtains the difference between the upper limit value and lower limit value of reflected pulse light received through a light-receiving-side optical fiber 17-2 as the intensity of the reflected pulse light. The reflected pulse light intensity is compared with a predetermined threshold value. If the reflected pulse light intensity exceeds the threshold value, it is determined that it begins to rain (rain sticks to a mirror surface 10-1).

In the above-described third and fourth embodiments, rain sticking to the mirror surface 10-1 is detected. With the same arrangement as described above, snow sticking to the mirror surface 10-1 can also be detected. With the same arrangement as described above, not only rain or snow but also dust or the like can also be detected.

Fifth Embodiment: S-Type

Figure 9:
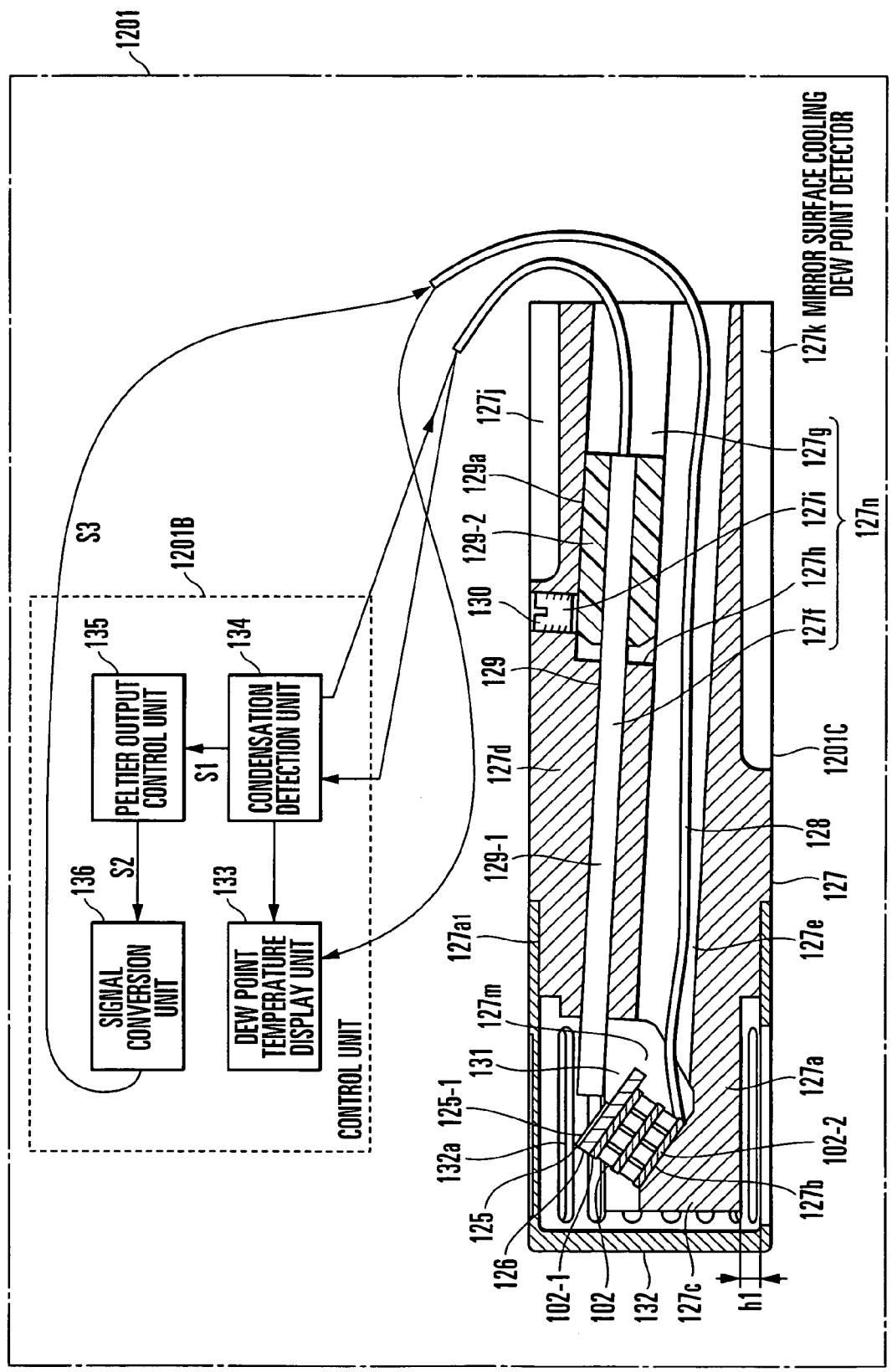
FIG. 9 is a schematic view showing the arrangement of a mirror surface cooling dew point detector (mirror surface cooling sensor) according to the fifth embodiment of the present invention.

FIG. 9 shows the schematic arrangement of a mirror surface cooling dew point detector according to the fifth embodiment of the present invention. A mirror surface cooling dew point detector 1201 has a sensor unit (mirror surface cooling sensor) 1201C and control unit 1201B. The mirror surface cooling sensor 1201C shown in FIG. 9 will be referred to as an S-type mirror surface cooling sensor herein.

In the S-type mirror surface cooling sensor 1201C, a mirror 125 is attached to a cooled surface 102-1 of a thermoelectric cooling element (Peltier element) 102. The mirror 125 is formed from, e.g., a silicon chip whose surface 125-1 is a mirror surface. A temperature detection element 126 made of, e.g., platinum is provided between the mirror 125 and the cooled surface 102-1 of the thermoelectric cooling element 102. The thermoelectric cooling element 102 having a heated surface 102-2 as the bottom surface is attached to an inclined surface 127b at a distal end portion 127a of a heat conductor 127 made of copper. The inclined surface 127b has a tilt angle of 30° to 45° with respect to the central axis of the heat conductor 127. Hence, the mirror surface 125-1 of the mirror 125 attached to the cooled surface 102-1 of the thermoelectric cooling element 102 is also tilted at 30° to 45° with respect to the central axis of the heat conductor 127.

Figure 10:
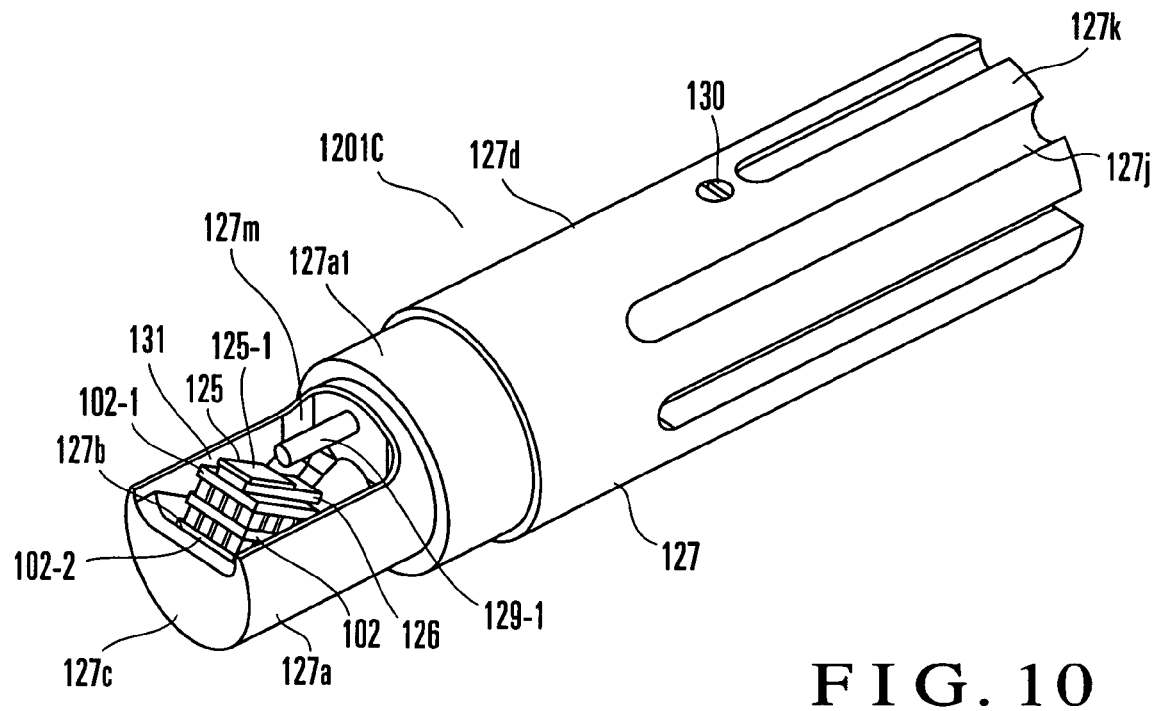
FIG. 10 is a perspective view showing the attached state of a thermoelectric cooling element at the distal end portion of a heat conductor.
Figure 11A:
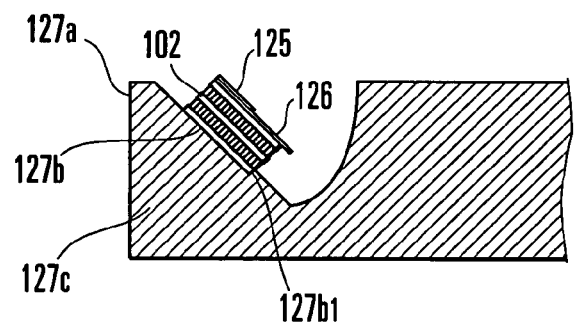
FIGS. 11A and 11B are schematic views for explaining the longitudinal- and lateral-direction aligned state of the thermoelectric cooling element on the inclined surface provided at the distal end portion of the heat conductor.
Figure 11B:
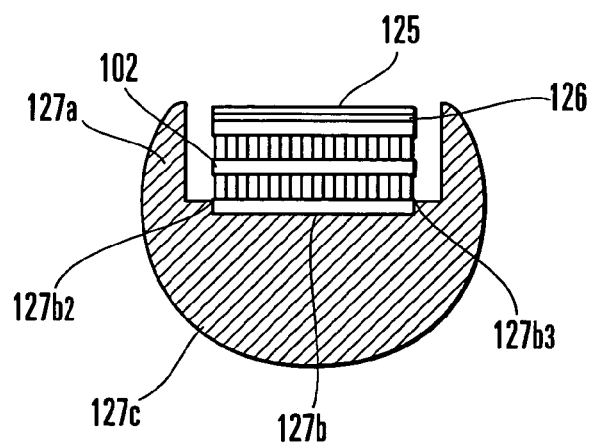

The inclined surface 127b at the distal end portion 127a of the heat conductor 127 is formed by cutting. That is, a chamber 127m to accommodated the thermoelectric cooling element 102 at the distal end portion 127a of the heat conductor 127 is formed by cutting. FIG. 10 shows the attached state of the thermoelectric cooling element 102 at the distal end portion 127a of the heat conductor 127. The heat conductor 127 has a cylindrical shape. The chamber 127m is formed by hollowing the distal end portion 127a by cutting. The thermoelectric cooling element 102 is fixed to the inclined surface 127b of the chamber 127m by solder or the like. The longitudinal alignment of the thermoelectric cooling element 102 on the inclined surface 127b is done by a step 127b1 provided midway on the inclined surface 127b, as schematically shown in FIG. 11A. The lateral alignment of the thermoelectric cooling element 102 on the inclined surface 127b is done by steps 127b2 and 127b3 provided on left and right sides on the inclined surface 127b, as schematically shown in FIG. 11B.

Figure 12:
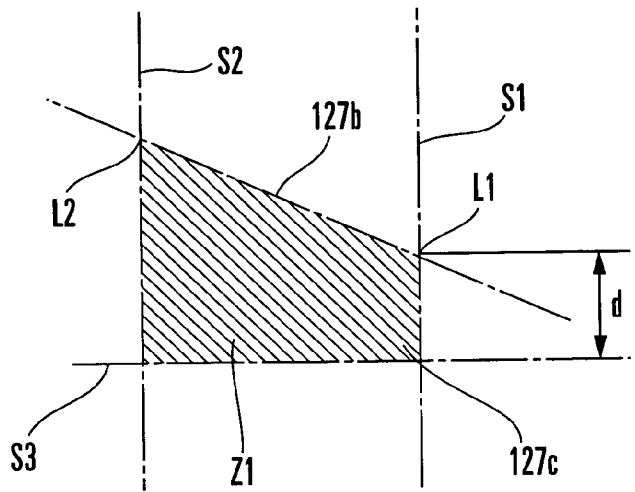
FIG. 12 is a view for explaining a thick portion provided under the inclined surface at the distal end portion of the heat conductor.

At the distal end portion 127a of the heat conductor 127, a thick portion 127c is present under the inclined surface 127b. More specifically, as shown in FIG. 12, the thick portion 127c in which the substance contained in the heat conductor 127 is present is arranged in a space Z1 surrounded by a first vertical surface S1 which crosses a leading edge L1 of the inclined surface 127b, a second vertical surface S2 which crosses a trailing edge L2 of the inclined surface 127b, a horizontal surface S3 which is spaced apart from the leading edge L1 of the inclined surface 127b by at least a predetermined distance d and crosses the vertical surfaces S1 and S2, and the inclined surface 127b.

A through hole 127e through which a lead wire 128 to the thermoelectric cooling element 102 passes is provided in a trunk 127d connected to the distal end portion 127a of the heat conductor 127. A holding portion 127n which holds an optical fiber 129 is formed integrally with the trunk 127d. In this embodiment, an optical fiber which has a small-diameter fiber portion 129-1 and a large-diameter fiber portion 129-2 connected to the small-diameter fiber portion 129-1 and whose light-projecting axis and light-receiving axis are parallel is used as the optical fiber 129. The structure of the optical fiber 129 will be described later. The lead wire 128 to the thermoelectric cooling element 102 includes a lead wire for current supply to the thermoelectric cooling element 102 and a lead wire for signal derivation from the temperature detection element 126.

In the heat conductor 127, the holding portion 127n for the optical fiber 129 comprises a through hole 127f, communicating hole (guide hole) 127g, wall (boundary between the through hole 127f and the communicating hole 127g) 127h, and threaded hole 127i. The small-diameter fiber portion 129-1 is inserted in the through hole 127f. The communicating hole 127g communicates with the through hole 127f and guides the large-diameter fiber portion 129-2. The wall 127h is located between the through hole 127f and the communicating hole 127g to regulate the sliding position of the large-diameter fiber portion 129-2 in the communicating hole 127g such that the tip of the small-diameter fiber portion 129-1 does not abut against the mirror surface 125-1 of the mirror 125. A screw 130 to fix the sliding position of the large-diameter fiber portion 129-2 in the communicating hole 127g to an arbitrary position is attached to the threaded hole 127i.

In this embodiment, the small-diameter fiber portion 129-1 of the optical fiber 129 is inserted from the rear side in the communicating hole 127g. The inserted small-diameter fiber portion 129-1 is inserted in the through hole 127f, thereby locating the large-diameter fiber portion 129-2 in the communicating hole 127g. The sliding position of the large-diameter fiber portion 129-2 in the communicating hole 127g is regulated by the wall 127h as a boundary between the through hole 127f and the communicating hole 127g. At the regulated position, a small gap is formed between the tip of the small-diameter fiber portion 129-1 and the mirror surface 125-1 of the mirror 125. Hence, in this embodiment, even when the large-diameter fiber portion 129-1 of the optical fiber 129 is fully slidably moved in the communicating hole 127g, the tip of the small-diameter fiber portion 129-1 can be prevented from abutting against the mirror surface 125-1 of the mirror 125.

The distance between the tip of the small-diameter fiber portion 129-1 and the mirror surface 125-1 of the mirror 125 can be adjusted by slidably moving the optical fiber 129 in the longitudinal direction. In this embodiment, after the distance between the tip of the small-diameter fiber portion 129-1 and the mirror surface 125-1 of the mirror 125 is adjusted, the screw 130 set in the threaded hole 127i from the outside of the heat conductor 127 is tightened, thereby fixing the sliding position of the large-diameter fiber portion 129-2 in the communicating hole 127g The through hole 127e in which the lead wire 128 to the thermoelectric cooling element 102 is inserted communicates with the communicating hole 127g included in the holding portion 127n for the optical fiber 129 behind the trunk 127d. For this reason, the sectional shape of the communicating hole 127g is not completely circular, and its lower end is partially cut. Even when the lower end is partially cut, the sectional shape of the communicating hole 127g is an arc equal to or larger than a semicircle. Hence, the large-diameter fiber portion 129-2 of the optical fiber 129 can slidably be moved without any problem.

In this embodiment, the central axes of the through hole 127e and the communicating hole 127g of the holding portion 127n for the optical fiber 129 are slightly tilted with respect to the central axis of the heat conductor 127. The optical fiber 129 is attached while tilting its optical axis with respect to the heat conductor 127 so that the large-diameter fiber portion 129-2 is located near the central portion of the heat conductor 127, and the small-diameter fiber portion 129-1 is located near the outer periphery of the heat conductor 127.

Semicircular recessed portions 127j are formed in the rear outer surface of the trunk 127d of the heat conductor 127. A three-dimensional pattern formed by the recessed portions 127j serves as a radiating portion 127k of the heat conductor 127. That is, in this embodiment, not only the holding portion 127n for the optical fiber 129 but also the radiating portion 127k is formed integrally with the heat conductor 127.

Figure 13:
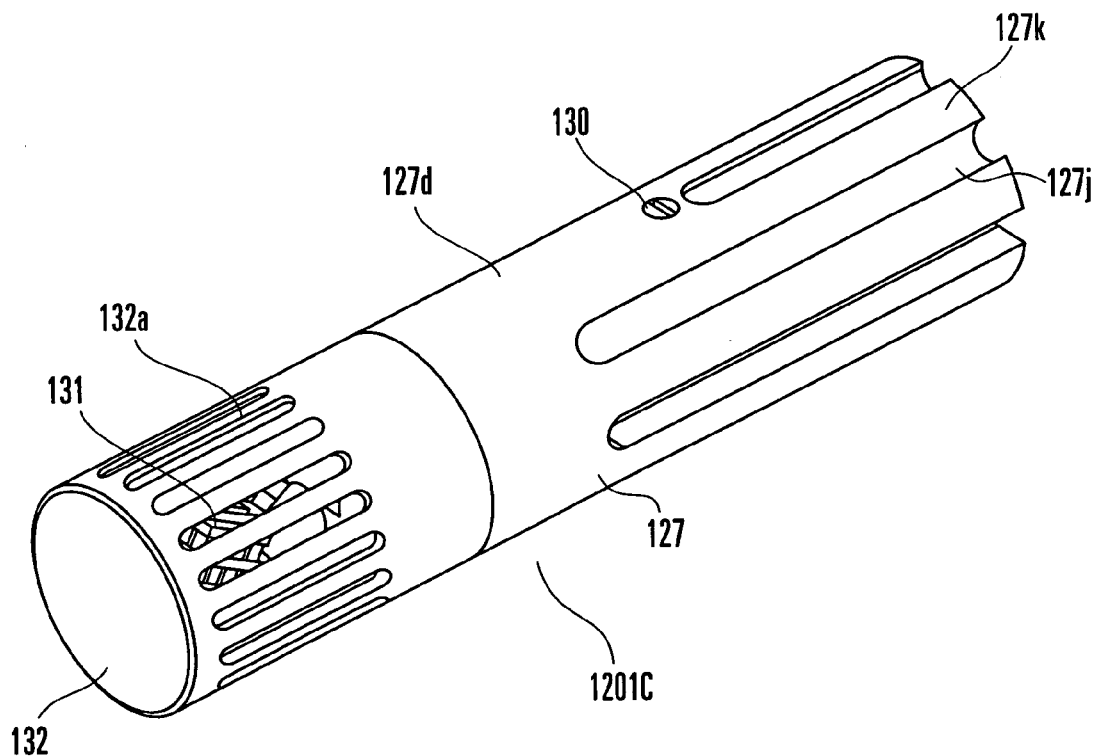
FIG. 13 is a perspective view showing an S-type mirror surface cooling sensor having a mirror cover attached to the detection unit.

A cylindrical mirror cover (cap) 132 having a closed end is attached to the distal end portion 127a of the heat conductor 127. More specifically, in this embodiment, a detection unit 131 having the thermoelectric cooling element 102 as the main constituent element is provided at the distal end portion 127a of the heat conductor 127, as shown FIG. 13. The detection unit 131 is covered with the mirror cover 132. The mirror cover 132 is made of a material having a high heat conduction. A plurality of vent holes 132a are formed in the side surface of the mirror cover 132. The mirror cover 132 is attached to the detection unit 131 by pressing the mirror cover 132 into a proximal portion 127a1 of the distal end portion 127a of the heat conductor 127. In this state, a small gap h1 (FIG. 9) is set between the inner surface of the mirror cover 132 and the outer surface of the distal end portion 127a of the heat conductor 127.

The mirror cover 132 is made of a material having a high heat conduction due to the following reasons. The detection unit 131 is placed in the target measurement gas. When the target measurement gas changes from a low temperature and low humidity to a high temperature and high humidity, condensation occurs on the mirror cover 132 if it is poor in heat conduction, and the water content cannot accurately be measured. Additionally, in measuring the target measurement gas at a high humidity, the entire structure must be heated to prevent condensation on the mirror cover 132. To uniformly heat the structure, the material preferably has a high heat conduction.

As described above, an optical fiber which has the small-diameter fiber portion 129-1 and the large-diameter fiber portion 129-2 connected to the small-diameter fiber portion 129-1 and whose light-projecting axis and light-receiving axis are parallel is used as the optical fiber 129. In this embodiment, by setting the light-projecting axis and light-receiving axis parallel, the light irradiation direction (light-projecting-side optical axis) from the tip of the small-diameter fiber portion 129-1 and the light-receiving direction (light-receiving-side optical axis) are made parallel. In addition, the light-projecting-side optical axis and light-receiving-side optical axis are adjacent at the same tilt angle. The small-diameter fiber portion 129-1 can have various forms as shown in FIGS. 3A to 3E.

The rear portion of the small-diameter fiber portion 129-1 is covered with a cylindrical sleeve 129a so that the large-diameter fiber portion 129-2 is formed. In this embodiment, the screw 130 is tightened from the outside of the heat conductor 127, thereby pressing the tip of the screw 130 against the large-diameter fiber portion 129-2. This pressing force is received by the sleeve 129a. Hence, any adverse effect on the optical fiber accommodated in the small-diameter fiber portion 129-1 can be prevented.

The control unit 1201B comprises a dew point temperature display unit 133, condensation detection unit 134, Peltier output control unit 135, and signal conversion unit 136. The temperature of the mirror 125 detected by the temperature detection element 126 is displayed on the dew point temperature display unit 133. The condensation detection unit 134 causes the optical fiber 129 to obliquely irradiate the mirror surface 125-1 of the mirror 125 with pulse light from the tip at a predetermined period. In addition, the condensation detection unit 134 obtains the difference between the upper limit value and lower limit value of reflected pulse light (scattered light) received through the optical fiber 129 as the intensity of the reflected pulse light and sends a signal S1 corresponding to the reflected pulse light intensity to the Peltier output control unit 135. Upon receiving the signal S1 from the condensation detection unit 134, the Peltier output control unit 135 compares the reflected pulse light intensity with a predetermined threshold value. If the reflected pulse light intensity is less than the threshold value, the Peltier output control unit 135 outputs, to the signal conversion unit 136, a control signal S2 to increase the current to the thermoelectric cooling element 102 in accordance with the value of the signal S1. If the reflected pulse light intensity exceeds the threshold value, the Peltier output control unit 135 outputs, to the signal conversion unit 136, the control signal S2 to decrease the current to the thermoelectric cooling element 102 in accordance with the value of the signal S1. The signal conversion unit 136 supplies, to the thermoelectric cooling element 102, a current S3 indicated by the control signal S2 from the Peltier output control unit 135.

Figure 14:
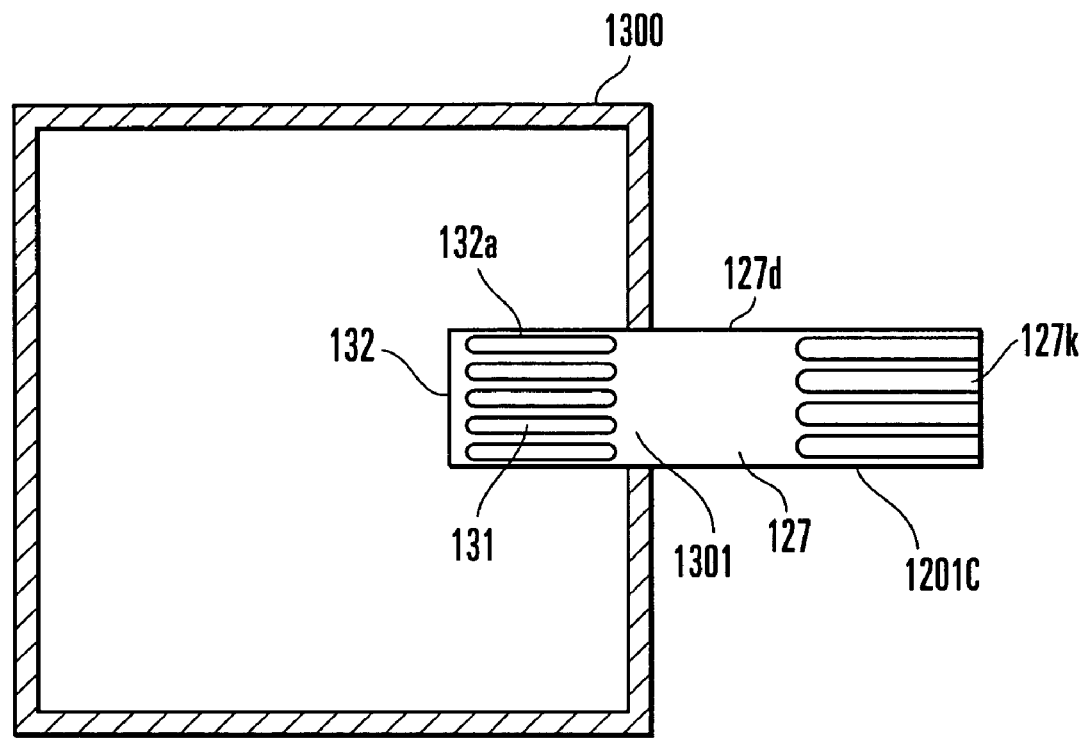
FIG. 14 is a view showing the attached state of the S-type mirror surface cooling sensor to a duct.

When the dew point of moisture in the target measurement gas flowing through, e.g., a duct is to be detected by the mirror surface cooling dew point detector 1201, the mirror surface cooling sensor 1201C is attached to a duct 1300, as shown in FIG. 14. More specifically, the detection unit 131 covered with the mirror cover 132 is inserted in an attachment hole 1301 formed in the side surface of the duct 1300. Although FIG. 14 does not illustrate the attachment structure of the mirror surface cooling sensor 1201C to the duct 1300, it can be attached to the duct 1300 by various methods by using, e.g., a bracket.

When the mirror surface cooling sensor 1201C is attached to the duct 1300, the detection unit 131 is located in the duct 1300, and the radiating portion 127k is located outside the duct 1300. The target measurement gas flowing through the duct 1300 enters the detection unit 131 through the vent holes 132a of the mirror cover 132. The mirror surface 125-1 of the mirror 125 is exposed to the target measurement gas. When the sensor is exposed to the target measurement gas, the thermoelectric cooling element 102 and mirror 125 of the detection unit 131 are protected by the mirror cover 132. In this case, since the small gap h1 is formed between the inner surface of the mirror cover 132 and the outer surface of the distal end portion 127a of the heat conductor 127, the target measurement gas enters the gap h1 and satisfactorily circulates at the detection unit 131.

When the mirror surface cooling sensor 1201C is attached to the duct 1300, the condensation detection unit 134 causes the optical fiber 129 to irradiate the mirror surface 125-1 of the mirror 125 with pulse light from the tip at a predetermined period, as shown in FIG. 5A. The mirror surface 125-1 is exposed to the target measurement gas. If no condensation occurs on the mirror surface 125-1, the pulse light emitted from the tip of the optical fiber 129 is almost wholly regularly reflected. The amount of reflected pulse light (scattered light) received from the mirror surface 125-1 through the optical fiber 129 is very small. Hence, when no condensation occurs on the mirror surface 125-1, the intensity of reflected pulse light received through the optical fiber 129 is low.

The condensation detection unit 134 obtains the difference between the upper limit value and lower limit value of the reflected pulse light received through the optical fiber 129 as the intensity of the reflected pulse light and sends the signal S1 corresponding to the reflected pulse light intensity to the Peltier output control unit 135. In this case, the reflected pulse light intensity is almost zero and less than the predetermined threshold value. For this reason, the Peltier output control unit 135 sends, to the signal conversion unit 136, the control signal S2 to increase the current to the thermoelectric cooling element 102. With this operation, the current S3 from the signal conversion unit 136 to the thermoelectric cooling element 102 increases, and the temperature of the cooled surface 102-1 of the thermoelectric cooling element 102 becomes low.

As the temperature of the cooled surface 102-1 of the thermoelectric cooling element 102, i.e., the temperature of the mirror 125 is decreased, vapor contained in the target measurement gas condenses on the mirror surface 125-1 of the mirror 125. The pulse light emitted from the tip of the optical fiber 129 is partially absorbed or diffused by the molecules of water. The intensity of the reflected pulse light (scattered light) received from the mirror surface 125-1 through the optical fiber 129 increases.

The condensation detection unit 134 obtains the difference between the upper limit value and lower limit value of each pulse of the received reflected pulse light as the intensity of the reflected pulse light. More specifically, as shown in FIG. 5B, a difference $\Delta L$ between an upper limit value Lmax and lower limit value Lmin of one pulse of the reflected pulse light is obtained as the intensity of the reflected pulse light. By the processing by the condensation detection unit 134, disturbance light $\Delta X$ contained in the reflected pulse light is removed. Hence, any operation error by disturbance light can be prevented. The processing scheme by the condensation detection unit 134 using pulse light to prevent any operation error by disturbance light is called a pulse modulation scheme. With this processing, the chamber to shield light from the mirror surface cooling sensor 1201C can be omitted from the mirror surface cooling dew point detector 1201.

If the intensity of the reflected pulse light received through the optical fiber 129 exceeds the threshold value, the Peltier output control unit 135 sends, to the signal conversion unit 136, the control signal S2 to decrease the current to the thermoelectric cooling element 102. With this operation, the decrease in temperature of the cooled surface 102-1 of the thermoelectric cooling element 102 is suppressed, and condensation is suppressed. When condensation is suppressed, the intensity of the reflected pulse light received through the optical fiber 129 becomes low. When the reflected pulse light intensity is less than the threshold value, the Peltier output control unit 135 sends, to the signal conversion unit 136, the control signal S2 to increase the current to the thermoelectric cooling element 102. By repeating this operation, the temperature of the cooled surface 102-1 of the thermoelectric cooling element 102 is adjusted so that the intensity of reflected pulse light received through the optical fiber 129 almost equals the threshold value. The adjusted temperature, i.e., the temperature (dew point temperature) at which condensation which has occurred on the mirror surface 125-1 reaches the equilibrium state is displayed on the dew point temperature display unit 133 as the dew point temperature.

In the dew point detection operation, in the mirror surface cooling sensor 1201C, when the temperature of the cooled surface 102-1 of the thermoelectric cooling element 102 decreases, the temperature of the heated surface 102-2 rises. Heat generated by the rising temperature of the heated surface 102-2 is transmitted from the inclined surface 127b at the distal end portion 127a of the heat conductor 127 through the trunk 127d and dissipated from the radiating portion 127k located outside the duct 1300.

In this embodiment, the heat conductor 127 has a large volume because the holding portion 127n for the optical fiber 129 and the radiating portion 127k are integrated. In addition, since the heat conductor 127 has no joints to the holding portion and radiating portion, no heat reservoir is generated at such joints. With this structure, a high heat dissipation effect can be obtained, and more heat can be moved to the cool side and dissipated without using any heat pipe. Furthermore, the holding portion and radiating portion are not necessary as separate components. For this reason, the number of components can be decreased. The cost can also be reduced because no heat pipe is used.

In this embodiment, the optical fiber 129 is attached not parallelly but slightly obliquely with respect to the central axis of the heat conductor 127. The large-diameter fiber portion 129-2 is located near the central portion of the heat conductor 127, and the small-diameter fiber portion 129-1 is located near the outer periphery of the heat conductor 127. Hence, the outer peripheral portion of the heat conductor 127 can be made thick. With this structure, the outer diameter of the heat conductor 127 decreases, and size reduction can be implemented.

In this embodiment, assembly, detachment, or position adjustment of the optical fiber 129 is easy. More specifically, to assemble the optical fiber 129, the small-diameter fiber portion 129-1 is inserted from the rear side of the communicating hole 127g. The inserted small-diameter fiber portion 129-1 is inserted in the through hole 127f to locate the large-diameter fiber portion 129-2 in the communicating hole 127g. The screw 130 set in the threaded hole 127i is tightened from the outside of the heat conductor 127. To adjust the position of the optical fiber 129, i.e., adjust the distance between the tip of the small-diameter fiber portion 129-1 and the mirror surface 125-1 of the mirror 125, the screw 130 is loosened from the outside of the heat conductor 127, and the optical fiber 129 is slidably moved in the longitudinal direction. To detach the optical fiber 129, the screw 130 is loosened from the outside of the heat conductor 127, and the optical fiber 129 is pulled from the rear side of the communicating hole 127g.

In this embodiment, the formation portion of the inclined surface 127b to which the thermoelectric cooling element 102 is attached at the distal end portion 127a of the heat conductor 127 hardly deforms due to vibration or external force because the thick portion 127c is formed under the inclined surface 127b. Especially, since the thick portion 127c is formed under the inclined surface 127b, the angle of the mirror surface 125-1 does not change even when small vibration or external force is applied. Hence, any adverse effect on the detection accuracy can be prevented.

In this embodiment, since the thick portion 127c is formed under the inclined surface 127b, the volume of the heat conductor 127 near the contact to the thermoelectric cooling element 102 is large. For this reason, the cooling capability (heat dissipation capability) can be increased while implementing size reduction of the sensor. In this embodiment, the thick portion 127c in which the substance contained in the heat conductor 127 is present is arranged in the space Z1 (FIG. 12) under the inclined surface 127b. However, the substance contained in the heat conductor 127 need not always fill the entire space Z1, and a small gap may be formed. The substance contained in the heat conductor 127 may be present outside the space Z1. In the present invention, even such a state is also defined as the state in which the substance contained in the heat conductor 127 is present in the space Z1.

In this embodiment, the chamber 127m including the inclined surface 127b at the distal end portion 127a of the heat conductor 127 is formed by cutting. However, the chamber 127m need not always be formed by cutting. The entire heat conductor 127 may be formed by using a mold or the like. In this embodiment, the heat conductor 127 is made of copper so that the chamber 127m can easily be formed by cutting. In addition, cutting is suitable for small production, and the cost can consequently be reduced. The heat conductor 127 need not always be made of copper, and for example, aluminum may be used.

Sixth Embodiment: L-Type

Figure 15:
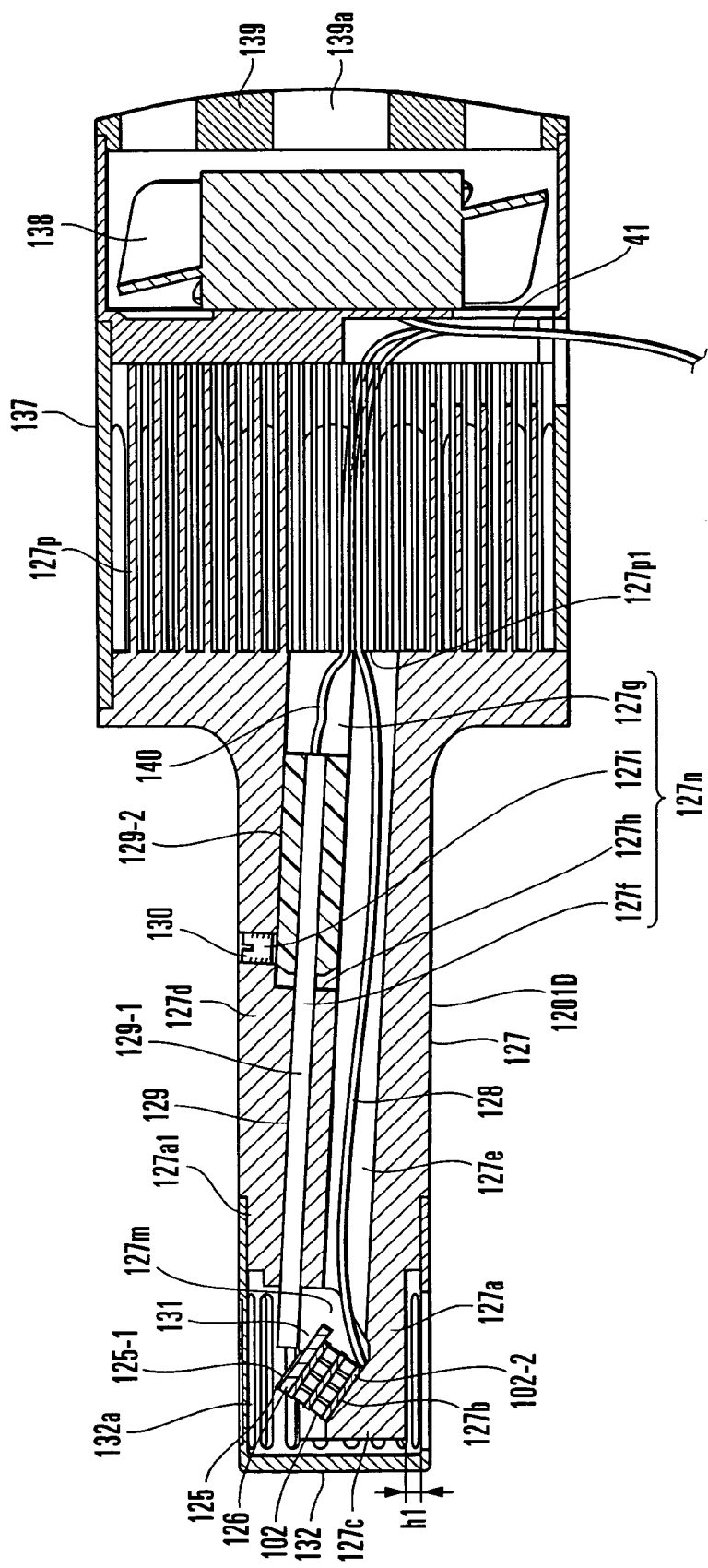
FIG. 15 is a schematic view showing the arrangement of a mirror surface cooling dew point detector (mirror surface cooling sensor) according to the sixth embodiment of the present invention.

FIG. 15 shows the structure of a mirror surface cooling sensor according to the sixth embodiment of the present invention. A mirror surface cooling sensor 1201D shown in FIG. 15 will be referred to as an L-type mirror surface cooling sensor herein. The L-type mirror surface cooling sensor 1201D is connected to a control unit 1201B to form a mirror surface cooling dew point detector 1201, like the S-type mirror surface cooling sensor 1201C of the fifth embodiment. The same reference numerals as in FIG. 9 denote the same or similar constituent elements in FIG. 15, and a description thereof will be omitted.

Figure 16:
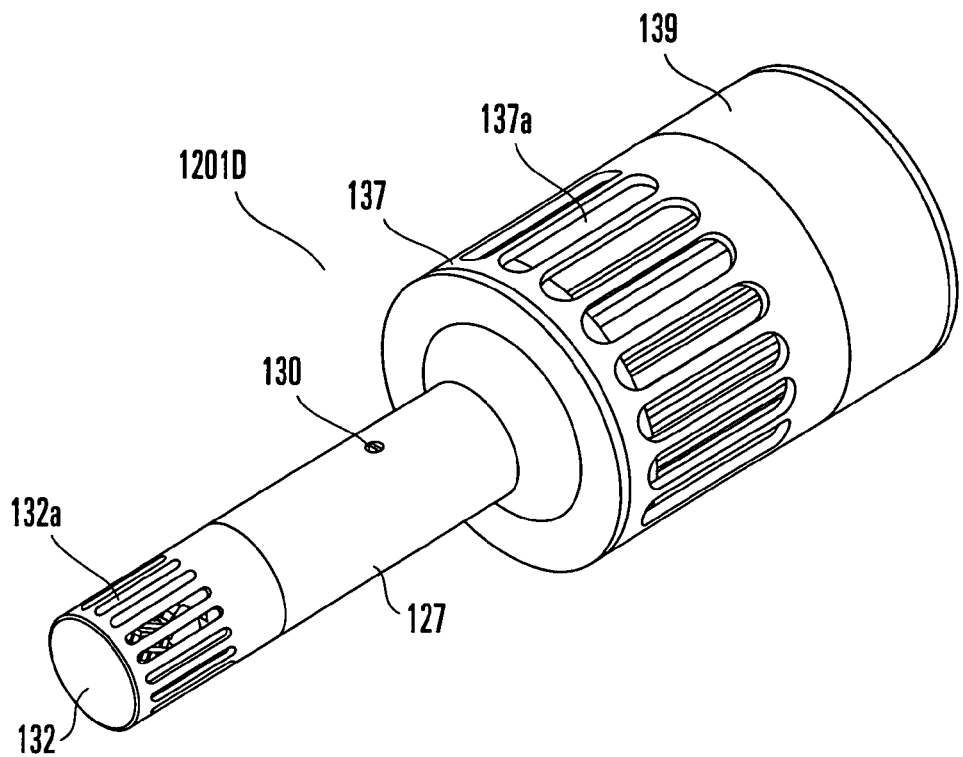
FIG. 16 is a perspective view showing an L-type mirror surface cooling sensor having a mirror cover attached to the detection unit.

The L-type mirror surface cooling sensor 1201D has the same basic structure as the S-type except the structure of a radiating portion. In the S-type mirror surface cooling sensor 1201C, the semicircular recessed portions 127j are formed behind the trunk 127d of the heat conductor 127, thereby forming the radiating portion 127k. In the L-type mirror surface cooling sensor 1201D, however, a large-diameter radiating fin 127p is integrally formed behind of a trunk 127d of a heat conductor 127. The radiating fin 127p is covered with a fin cover 137. As shown in FIG. 16, vent holes 137a are provided in the side surface of the fin cover 137.

Figure 17:
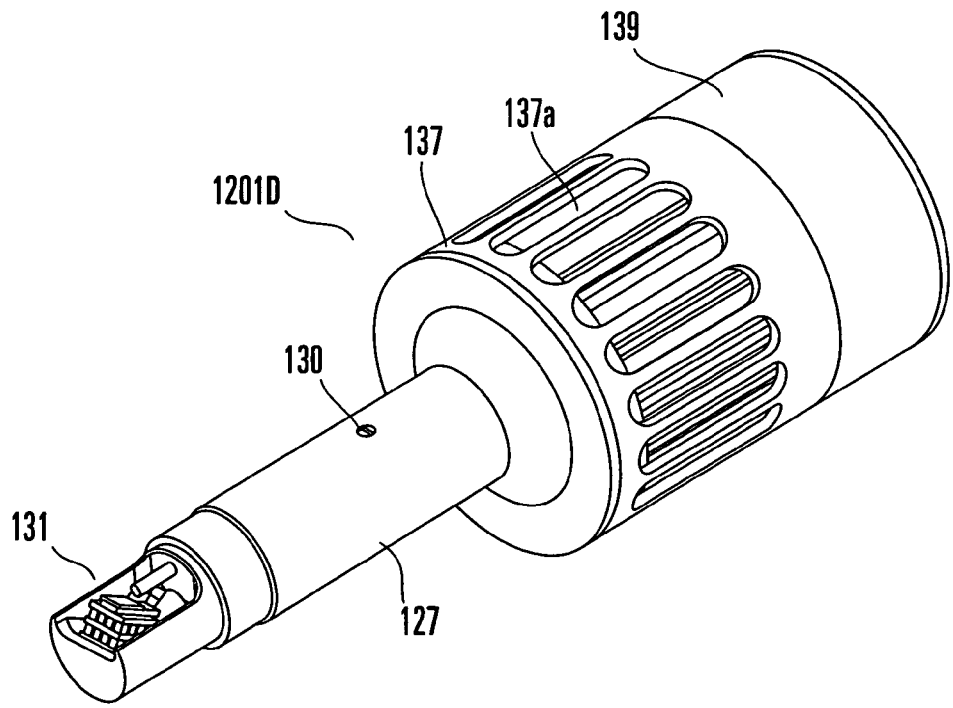
FIG. 17 is a perspective view showing the L-type mirror surface cooling sensor before the mirror cover is attached.
Figure 18:
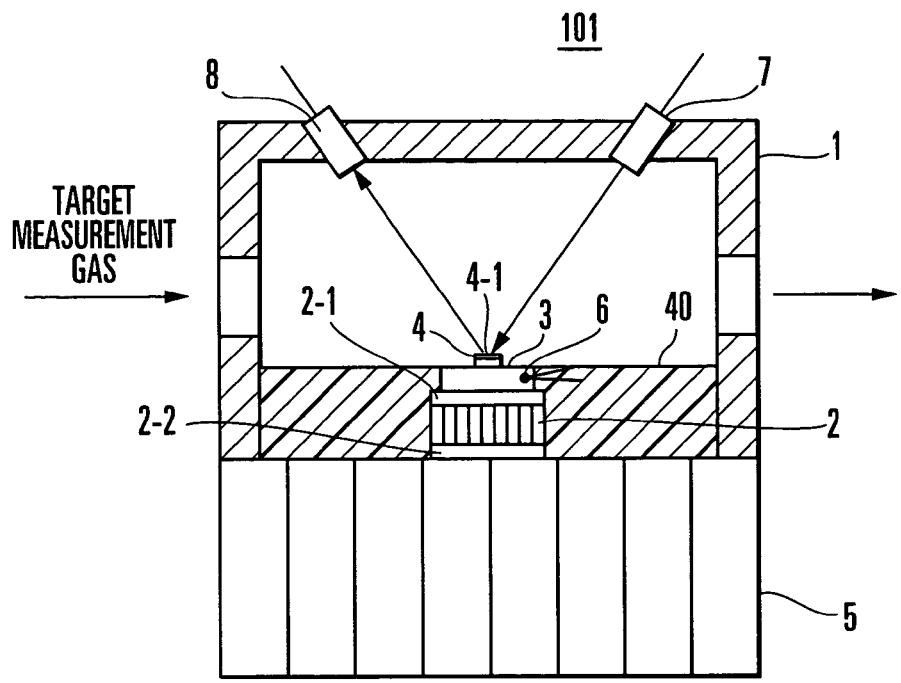
FIG. 18 is a view showing the main part of a conventional mirror surface cooling dew point detector which employs the regular-reflected light detection method.
Figure 19:
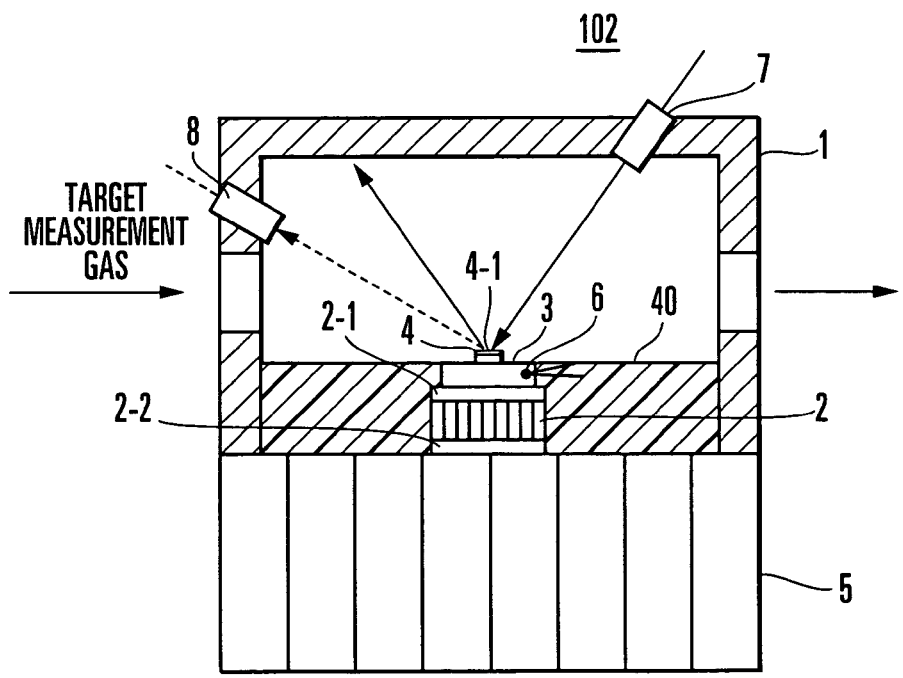
FIG. 19 is a view showing the main part of another conventional mirror surface cooling dew point detector which employs the scattered light detection method.
Figure 20:
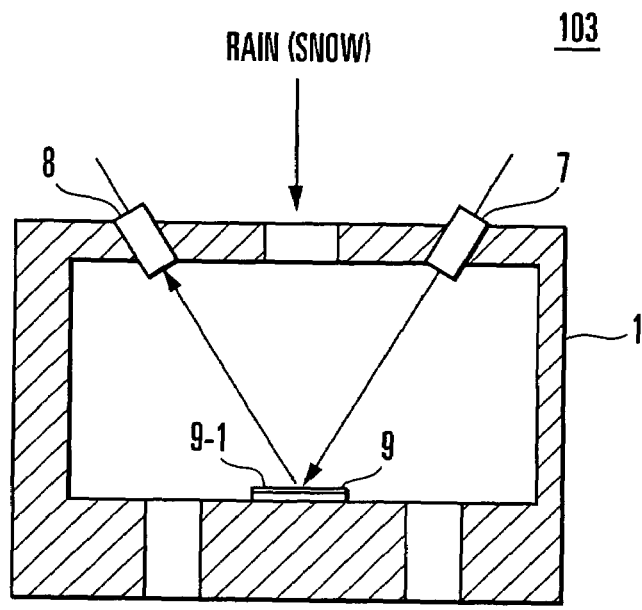
FIG. 20 is a view showing the main part of a conventional weather detector which employs the regular-reflected light detection method.
Figure 21:
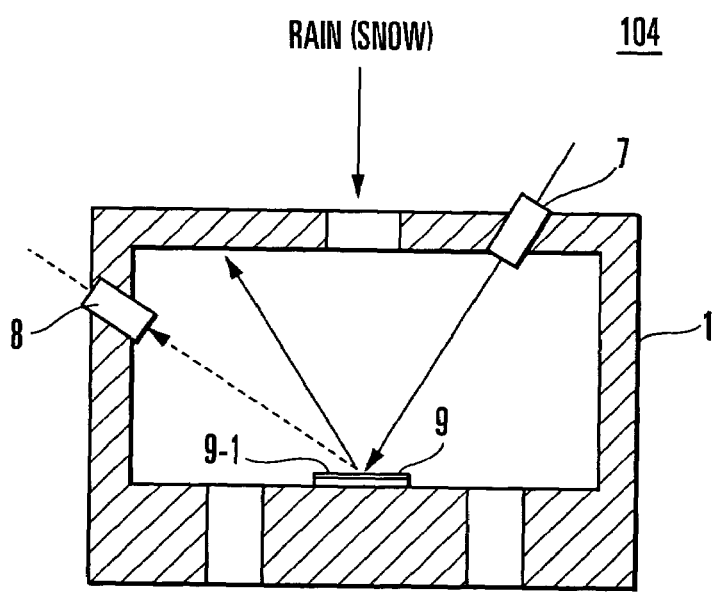
FIG. 21 is a view showing the main part of another conventional weather detector which employs the scattered light detection method.
Figure 22:
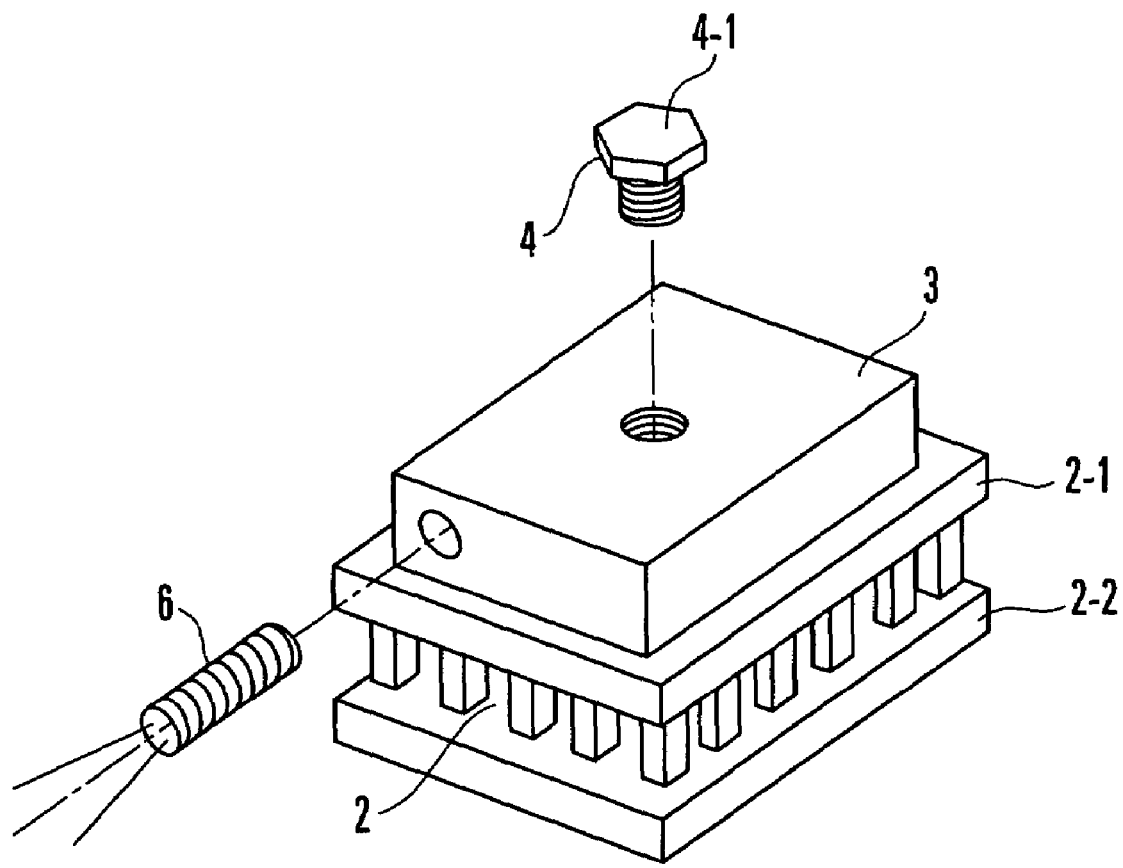
FIG. 22 is a perspective view showing the attachment structure of the mirror and temperature detection element in the conventional mirror surface cooling dew point detector.

In addition, a cooling fan 138 is provided behind the radiating fin 127p. A fan cover 139 is attached to the rear portion of the cooling fan 138. A plurality of vent holes 139a are formed in the fan cover 139. A through hole 127p1 in which a lead wire 128 to a thermoelectric cooling element 102 and a fiber line 140 to an optical fiber 129 are inserted is provided at the central portion of the radiating fin 127p. A wire hole in which the lead wire 128 to the thermoelectric cooling element 102, the fiber line 140 to the optical fiber 129, and a lead wire 141 to the fan 138 are inserted is formed in the fin cover 137. FIG. 17 shows the mirror surface cooling sensor 1201D before a mirror cover 132 is attached. As is apparent from FIG. 17, the structure of a detection unit 131 is the same as in the S-type mirror surface cooling sensor 1201C. The dew point temperature is measured on the basis of the same principle as the S-type.

In the L-type mirror surface cooling sensor 1201D, the large-diameter radiating fin 127p is integrally formed behind the trunk 127d of the heat conductor 127. The cooling fan 138 rotates behind the radiating fin 127p. By rotation of the cooling fan 138, outside cool air is drawn into the fan cover 139 through the vent holes 139a of the fan cover 139. This air passes through the spaces in the radiating fin 127p and is forcibly exhausted from the vent holes 137a of the fin cover 137. With this operation, the radiating fin 127p in the fin cover 137 is forcibly cooled, the radiation efficiency increases, and the cooling performance is increased.

In the above-described fifth or sixth embodiment, the distal end portion 127a of the heat conductor 127 is covered with the mirror cover 132. However, if there is no risk of foreign substance invasion, the mirror cover 132 need not always be used. In the above-described fifth or sixth embodiment, the mirror cover 132 is pressed into the distal end portion 127a of the heat conductor 127. Instead, the mirror cover 132 may be threadably engaged with the proximal portion 127a1 of the distal end portion 127a of the heat conductor 127. Referring to FIG. 15, the fin cover 137, cooling fan 138, and fan cover 139 may be removed.

According to the present invention, the optical axis of the light-receiving means and that of the light-emitting means are arranged adjacent in almost parallel at almost the same tilt angle. Hence, the light-emitting means and light-receiving means can be attached to one point, and size reduction can be prompted. In addition, since the optical axis of the light-emitting means and that of the light-receiving means are arranged adjacent in almost parallel at almost the same tilt angle, alignment is easy, and the workability in assembly increases.

An optical fiber which has a small-diameter fiber portion and large-diameter fiber portion and whose light-projecting axis and light-receiving axis are parallel is used as the light-projecting means and light-receiving means. The optical fiber holding portion (through hole, communicating hole, wall, and engaging portion) is provided integrally with the heat conductor. An engaging member to fix the sliding position of the large-diameter fiber portion in the communicating hole is detachably attached from the outside of the heat conductor. With this arrangement, assembly, detachment, or position adjustment of the optical fiber is easy. In addition, a high heat dissipation effect can be obtained, the number of components can be decreased, and the cost can also be reduced.

A thick portion in which the substance contained in the heat conductor is present is arranged in a space surrounded by the first vertical surface which crosses the leading edge of the inclined surface, the second vertical surface which crosses the trailing edge of the inclined surface, the horizontal surface which is spaced apart from the leading edge of the inclined surface by at least a predetermined distance and crosses the first and second vertical surfaces, and the inclined surface. With this structure, the angle of the mirror surface does not change even when small vibration or external force is applied. Hence, any adverse effect on the detection accuracy can be prevented.

Since the heat conductor has the integrated structure of the holding portion and radiating portion, a high heat dissipation effect can be obtained, the number of components can be decreased, and the cost can also be reduced.

What is claimed is:

1. A moisture detection device comprising:
   a mirror whose mirror surface is exposed to a target measurement gas;
   cooling means for cooling said mirror;
   light-projecting means for obliquely irradiating a mirror surface of the mirror with light;
   light-receiving means, arranged adjacent to said light-projecting means to have an optical axis substantially parallel to an optical axis of said light-projecting means and a tilt angle substantially equal to a tilt angle of said light-projecting means, for receiving scattered light of the light emitted from said light-projecting means to the mirror surface;
   moisture detection means for detecting moisture generated on the mirror surface of said mirror cooled by said cooling means, on the basis of the scattered light received by said light-receiving means;
   wherein said cooling means comprises a thermoelectric cooling element whose low-temperature-side surface is attached to a surface on an opposite side of the mirror surface of said mirror,
   said moisture detection means comprises a heat conductor to which a high-temperature-side surface of said thermoelectric cooling element is attached,
   said light-projecting means and said light-receiving means each comprise an optical fiber whose light-projecting axis and light-receiving axis are parallel to each other,
   said optical fibers being in a tube comprising a small-diameter fiber portion and a large-diameter fiber portion connected to said small-diameter fiber portion, and
   said heat conductor comprises
   a through hole through which said small-diameter fiber portion is inserted,
   a guide hole which communicates with the through hole to guide said large-diameter fiber portion,
   a locking portion which regulates a position of said large-diameter fiber portion in the guide hole not to make a tip of said small-diameter fiber portion but against the mirror surface of said mirror,
   an engaging member which is attached into the guide hole from an outside of said heat conductor to fix said large-diameter fiber portion by a tip.

2. A device according to claim 1, wherein said tube is inserted while tilting an optical axis with respect to a central axis of said heat conductor.

3. A moisture detection device comprising:
   a mirror whose mirror surface is exposed to a target measurement gas;
   cooling means for cooling said mirror;
   light-projecting means for obliquely irradiating a mirror surface of the mirror with light;
   light-receiving means, arranged adjacent to said light-projecting means to have an optical axis substantially parallel to an optical axis of said light-projecting means and a tilt angle substantially equal to a tilt angle of said light-projecting means, for receiving scattered light of the light emitted from said light-projecting means to the mirror surface;
   moisture detection means for detecting moisture generated on the mirror surface of said mirror cooled by said cooling means, on the basis of the scattered light received by said light-receiving means;
   wherein said cooling means comprises a thermoelectric cooling element whose low-temperature-side surface is attached to a surface on an opposite side of the mirror surface of said mirror,
   said moisture detection means comprises a heat conductor to which a high-temperature-side surface of said thermoelectric cooling element is attached,
   said light-projecting means and said light-receiving means each comprise an optical fiber whose light-projecting axis and light-receiving axis are parallel to each other,
   said heat conductor comprises
   an inclined surface to which said thermoelectric cooling element is attached, and
   a thick portion which is made of a substance contained in said heat conductor and is surrounded by said inclined surface, a first vertical surface which crosses a leading edge of said inclined surface, a second vertical surface which crosses a trailing edge of said inclined surface, and a horizontal surface which is spaced apart from the leading edge of said inclined surface by at least a predetermined distance in a direction parallel to the first vertical surface and crosses the first vertical surface and second vertical surface.

4. A device according to claim 3, wherein said inclined surface is formed by cutting a distal end portion of said heat conductor having a cylindrical shape.

5. A moisture detection device comprising:
a mirror whose mirror surface is exposed to a target measurement gas;
cooling means for cooling said mirror;
light-projecting means for obliquely irradiating a mirror surface of the mirror with light;
light-receiving means, arranged adjacent to said light-projecting means to have an optical axis substantially parallel to an optical axis of said light-projecting means and a tilt angle substantially equal to a tilt angle of said light-projecting means, for receiving scattered light of the light emitted from said light-projecting means to the mirror surface;
moisture detection means for detecting moisture generated on the mirror surface of said mirror cooled by said cooling means, on the basis of the scattered light received by said light-receiving means;
wherein said cooling means comprises a thermoelectric cooling element whose low-temperature-side surface is attached to a surface on an opposite side of the mirror surface of said mirror,
said moisture detection means comprises a heat conductor to which a high-temperature-side surface of said thermoelectric cooling element is attached,
said light-projecting means and said light-receiving means each comprise an optical fiber whose light-projecting axis and light-receiving axis are parallel to each other,
said heat conductor comprises
a holding portion which holds said light-projecting means and light-receiving means, and
a heat radiating portion which is made of the same material as said holding portion and dissipates heat from the high-temperature-side surface of said thermoelectric cooling at a position spaced apart from said thermoelectric cooling element.

* * * * *